United States Patent
Edd et al.

(10) Patent No.: US 12,385,908 B2
(45) Date of Patent: Aug. 12, 2025

(54) SIZE-BASED PARTICLE SEPARATION AND CONCENTRATION USING PARTICLE SIZE AMPLIFICATION

(71) Applicant: The General Hospital Corporation, Boston, MA (US)

(72) Inventors: Jon F. Edd, Wakefield, MA (US); Kaja Kaastrup, Charlestown, MA (US); Ravi Kapur, Sharon, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 968 days.

(21) Appl. No.: 17/417,879

(22) PCT Filed: Dec. 26, 2019

(86) PCT No.: PCT/US2019/068565
§ 371 (c)(1),
(2) Date: Jun. 24, 2021

(87) PCT Pub. No.: WO2020/139936
PCT Pub. Date: Jul. 2, 2020

(65) Prior Publication Data
US 2022/0074932 A1 Mar. 10, 2022

Related U.S. Application Data

(60) Provisional application No. 62/785,550, filed on Dec. 27, 2018.

(51) Int. Cl.
*G01N 33/543* (2006.01)
*B01L 3/00* (2006.01)
*G01N 33/49* (2006.01)

(52) U.S. Cl.
CPC .. *G01N 33/54366* (2013.01); *B01L 3/502761* (2013.01); *G01N 33/491* (2013.01);
(Continued)

(58) Field of Classification Search
None
See application file for complete search history.

(56) References Cited

U.S. PATENT DOCUMENTS

| 5,968,820 A | 10/1999 | Zborowski et al. |
| 6,540,896 B1 | 4/2003 | Manz et al. |

(Continued)

OTHER PUBLICATIONS

Di Carlo et al., "Continuous inertial focusing, ordering, and separation of particles in microchannels.," Proc. Natl. Acad. Sci. U.S.A., Nov. 2007, 104(48):18892-18897.
(Continued)

*Primary Examiner* — Brian R Gordon
(74) *Attorney, Agent, or Firm* — Fish & Richardson P.C.

(57) ABSTRACT

Methods of using particle size amplification to facilitate size-based particle separation and concentration. At least one of the methods includes introducing a plurality of binding moieties into a fluid sample; allowing at least one of the binding moieties to bind two or more biological particles to form a particle cluster, in which the particle cluster includes a first type of biological particle bound to a second different type of biological particle; and flowing the fluid sample including the particle cluster into a particle sorting region of a microfluidic device.

19 Claims, 13 Drawing Sheets

(52) U.S. Cl.
CPC .................. *G01N 33/54313* (2013.01); *B01L 2200/0652* (2013.01); *B01L 2300/0636* (2013.01); *B01L 2300/0816* (2013.01); *B01L 2400/086* (2013.01)

(56) References Cited

U.S. PATENT DOCUMENTS

| | | | |
|---|---|---|---|
| 6,767,706 B2 | 7/2004 | Quake et al. | |
| 8,137,912 B2 | 3/2012 | Kapur et al. | |
| 8,895,298 B2* | 11/2014 | Toner | G01N 33/54386 435/372 |
| 9,034,658 B2 | 5/2015 | Barber et al. | |
| 9,895,694 B2* | 2/2018 | Kapur | B01L 3/502746 |
| 10,478,819 B2* | 11/2019 | Kapur | B01L 3/502746 |
| 10,875,021 B2* | 12/2020 | Kapur | B01L 3/502761 |
| 11,027,280 B2* | 6/2021 | Kapur | B01L 3/502746 |
| 11,944,971 B2* | 4/2024 | Kapur | A61K 35/28 |
| 2005/0121604 A1* | 6/2005 | Mueth | A61M 1/3681 250/251 |
| 2007/0059716 A1* | 3/2007 | Balis | B01L 3/502753 435/6.12 |
| 2007/0059719 A1* | 3/2007 | Grisham | B01L 3/502753 705/2 |
| 2007/0059781 A1* | 3/2007 | Kapur | B01L 3/502746 702/19 |
| 2007/0099207 A1* | 5/2007 | Fuchs | B01L 3/502753 435/6.16 |
| 2009/0032449 A1* | 2/2009 | Mueth | H05H 3/04 210/94 |
| 2013/0209988 A1* | 8/2013 | Barber | G01N 33/56972 435/7.25 |
| 2016/0121331 A1* | 5/2016 | Kapur | A61K 35/28 435/309.1 |
| 2016/0123857 A1 | 5/2016 | Kapur et al. | |
| 2016/0123858 A1* | 5/2016 | Kapur | G01N 15/1484 73/61.71 |
| 2018/0161775 A1* | 6/2018 | Kapur | G01N 1/4077 |
| 2018/0361384 A1* | 12/2018 | Kapur | G01N 15/0618 |
| 2019/0137931 A1* | 5/2019 | Mueth | G03H 1/0005 |
| 2024/0052284 A1* | 2/2024 | Gachelin | C12M 41/36 |
| 2024/0198338 A1* | 6/2024 | Kapur | B01L 3/502761 |

OTHER PUBLICATIONS

Di Carlo et al., "Particle segregation and dynamics in confined flows," Phys. Rev. Lett., Mar. 2009, 102(9):094503-1-094503-4.
Di Carlo, "Inertial microfluidics," Lab Chip, 2009, 9(21):3038-3046.
International Prelminary Report on Patentability in International Appln. No. PCT/US2019/068565, mailed on Jul. 8, 2021, 7 pages.
International Seach Report and Written Opinion in International Appln. No. PCT/US2019/068565, mailed on Mar. 4, 2020, 9 pages.
Lansdorp et al., "Cyclic tetramolecular complexes of monoclonal antibodies: a new type of cross-linking reagent," Eur J Immunol, Jun. 1986, 16(6):679-683.
Laurell et al., "Chip integrated strategies for acoustic separation and manipulation of cells and particles," Chemical Society Reviews, 2007, 36:492-506.
Li et al., "A review of microfabrication techniques and dielectrophoretic microdevices for particle manipulation and separation," Journal of Physics D: Applied Physics, 2014, 47(6):063001, 56 pages.
McGrath et al., "Deterministic lateral displacement for particle separation: a review," Lab Chip, Nov. 2014, 14(21):4139-58.
Wognum et al., "Use of Tetrameric Antibody Complexes to Stain Cells for Flow Cytometry," Cytometry, 1987, 8:366-71.

* cited by examiner

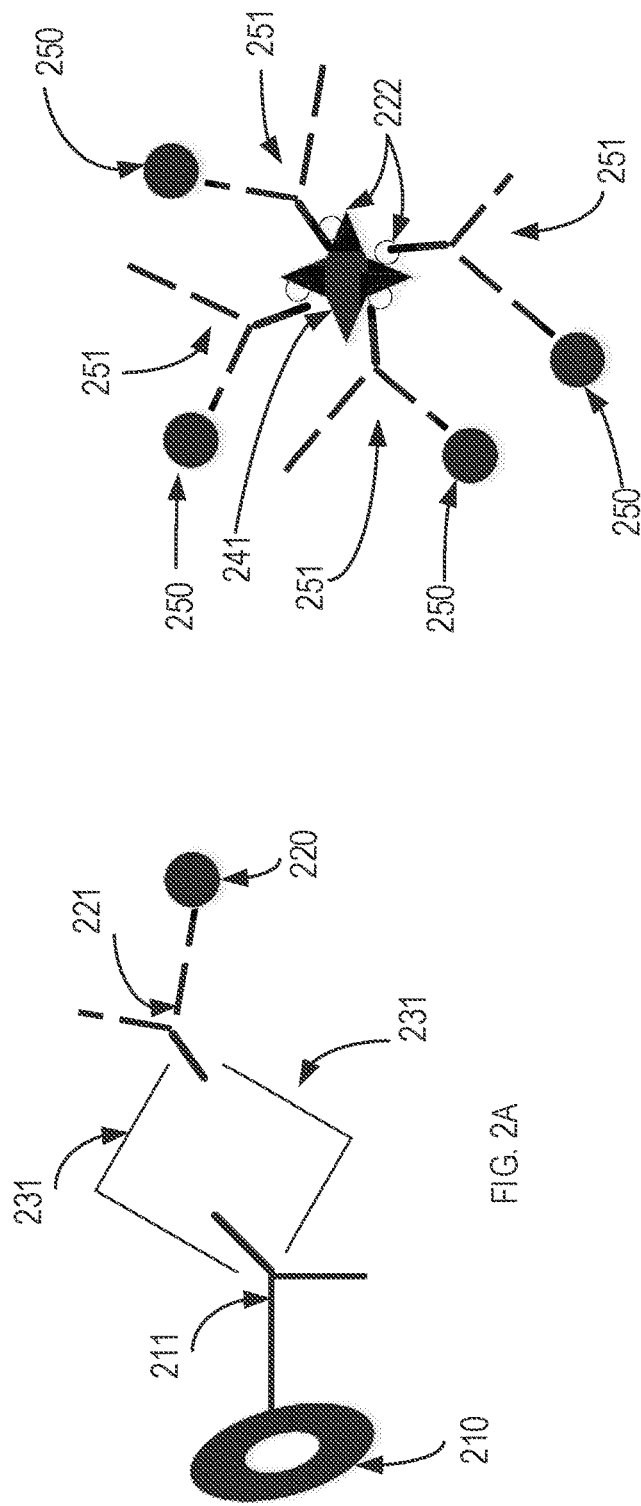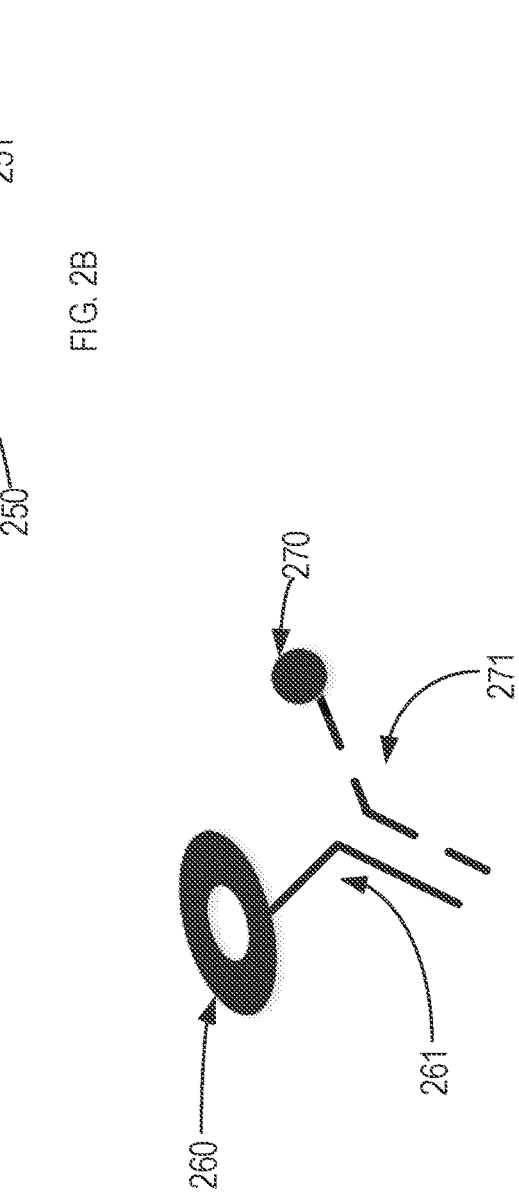

| Trial (flow rate=80 µL/min) | Platelet depletion (%) | Bacteria yield (%) |
|---|---|---|
| 1. 2.4x10⁸ PLT/mL | 60 | - |
| 2. 1.9x10⁸ PLT/mL | 70 | - |
| 3. 1.9x10⁸ PLT/mL | 80 | 70 |
| 4. Double TAC concentration (1.9x10⁸ PLT/mL) | 94 | - |

FIG. 8C

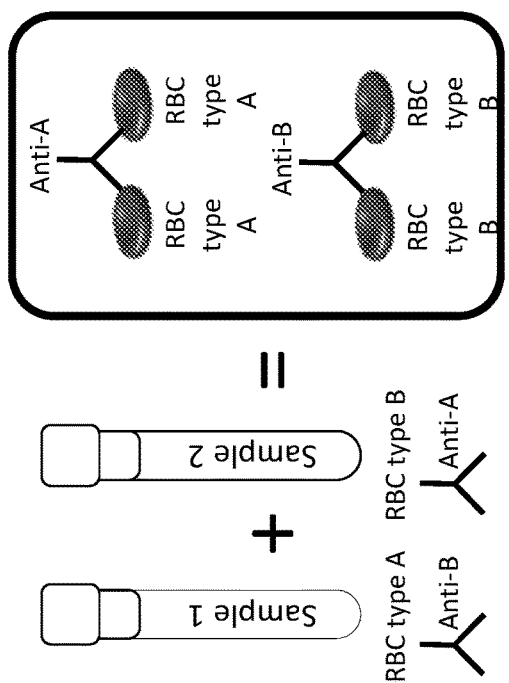
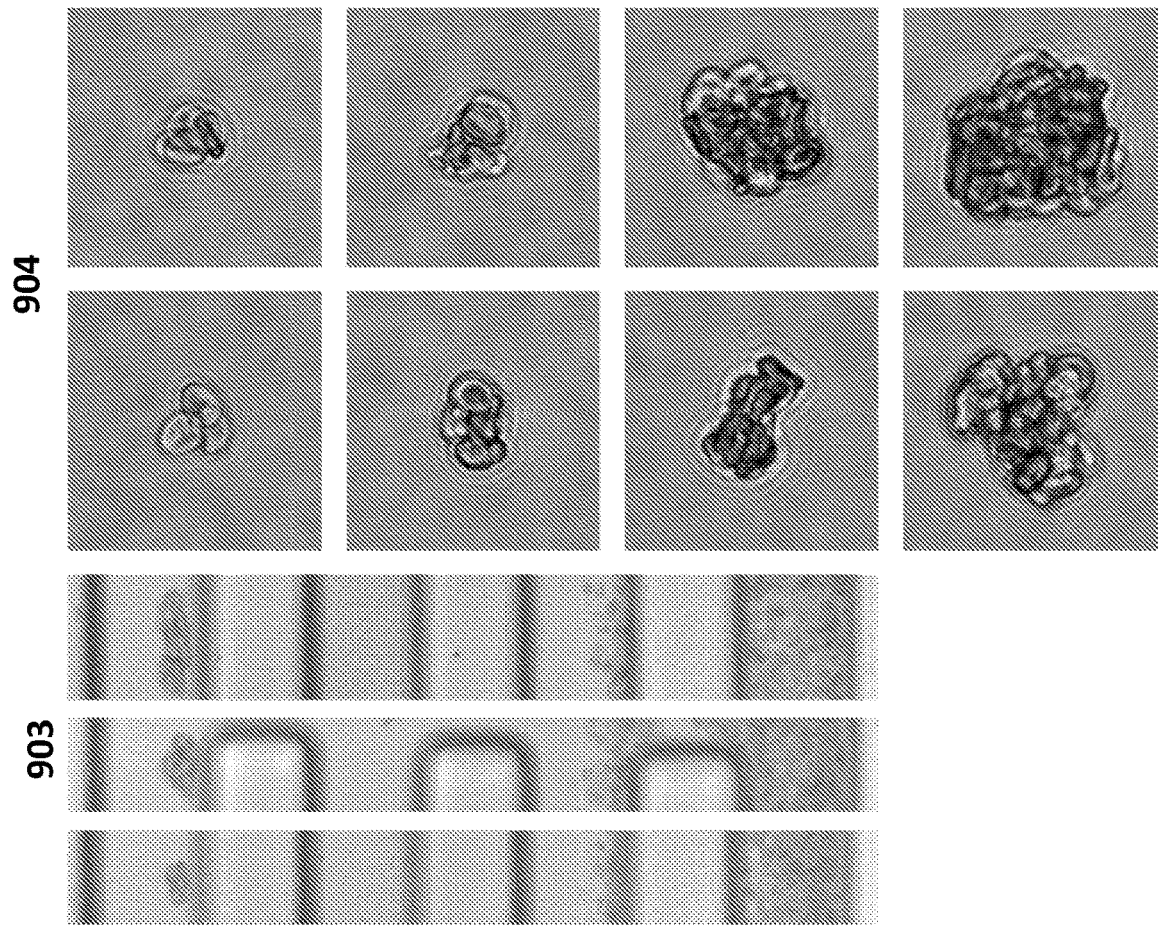
FIG. 9B

SIZE-BASED PARTICLE SEPARATION AND CONCENTRATION USING PARTICLE SIZE AMPLIFICATION

CROSS-REFERENCE TO RELATED APPLICATIONS

This application is a § 371 National Stage Application of PCT/US2019/068565, filed Dec. 26, 2019, which claims priority to U.S. Provisional Application Ser. No. 62/785,550, filed on Dec. 27, 2018, the entire contents of which are hereby incorporated by reference.

STATEMENT OF FEDERALLY SPONSORED RESEARCH

This invention was made with government support under Grant No. EB002503 awarded by the National Institutes of Health. The government has certain rights in the invention.

BACKGROUND

Particle separation and concentration have been used in numerous applications across industries and fields. Examples of such applications include chemical process and fermentation filtration, water purification/waste water treatment, sorting and filtering components of blood, concentrating colloid solutions, and purifying and concentrating environmental samples. Various macro-scale techniques have been developed for use in these applications, including methods such as centrifugation and filter-based techniques. Typically, such techniques may require systems that are large, bulky, and expensive, and may have complex moving components.

In certain cases, micro-scale techniques offer advantages over macro-scale techniques, in that scaling down allows the use of unique hydrodynamic effects for particle sorting and filtration. Therefore, these techniques can eliminate the need for large systems with complex moving components. Moreover, micro-scale techniques offer the possibility of portable devices capable of performing sorting and filtration at lower cost than larger macro-scale systems.

SUMMARY

This disclosure features methods and systems for separation and/or concentration using particle size amplification via particle complexing. The methods include using particle complexing techniques to amplify the size of particular biological particles such that separation of the particular biological particles from other particles can be easier to achieve when utilizing devices such as, for example, size-based particle sorters. The complexing involves forming one or more particle clusters using at least one binding moiety to bind the particular biological particles to one or more biological particles of similar size (including binding two or more of the particular biological particles to each other), or to bind the particular biological particles to other biological particles of a different size. The one or more particle clusters are then sent through a microfluidic sorting device or concentrating device where the particle clusters experience a size-dependent force such that they are separated from other biological particles of smaller size and/or concentrated within a fluid sample.

In one aspect, the present disclosure provides methods that include introducing a plurality of binding moieties into a fluid sample and allowing at least one of the binding moieties to bind two or more biological particles to form a particle cluster. The method includes flowing the fluid sample comprising the particle cluster into a particle sorting region of a microfluidic device. The particle sorting region divides the fluid sample into a first fluid stream within a first microfluidic channel and a second fluid stream within a second microfluidic channel, and wherein the particle cluster experiences a size-dependent force within the particle sorting region that is sufficient to maintain the particle cluster within the first fluid stream and away from the second fluid stream.

The particle cluster can include a first type of biological particle bound to a second different type of biological particle.

The fluid sample can include a third type of biological particle that is different from the first and second types of biological particles, and wherein the third type of biological particle wherein the third type of biological particle flows from the first fluid stream into the second fluid stream in the particle sorting region, and the size-dependent force within the particle sorting region is insufficient to maintain the third type of biological particle in the first fluid stream. The average size of the third type of biological particle within the fluid sample can be smaller than an average size of the particle cluster. An average size of the third type of biological particle within the fluid sample can be smaller than an average size of the particle cluster. An average size of the second type of biological particle can be smaller than an average size of the first type of biological particle. The average size of the second type of biological particle can be substantially the same as an average size of the third type of biological particle. The average size of the second type of biological particle can be smaller than an average size of the first type of biological particle. The fluid sample can include blood and the particle cluster can include at least one red blood cell and at least one platelet. The third type of biological particle can include a bacteria cell.

In some implementations, the particle sorting region includes a third microfluidic channel separated from the first microfluidic channel, and wherein the method comprises flowing a second fluid sample into the third microfluidic channel, wherein a portion of the second fluid sample flows from the third microfluidic channel into the first microfluidic channel in the particle sorting region, and the size-dependent force experienced by the particle cluster is sufficient to drive the particle cluster from the first fluid sample into the portion of the second fluid sample in the first microfluidic channel. The first fluid sample can include blood and the second fluid sample can include a buffer solution. The blood can be at least partially diluted.

The plurality of binding moieties can target at least one of anti-mouse IgG Fc antigens, anti-human CD41 antigens, and/or anti-human CD235a antigens. The plurality of binding moieties can include at least one of a polymer, an antibody, an antibody fragment, an aptamer, and/or a tetrameric antibody complex. The plurality of binding moieties can include a recombinant protein. A first binding moiety can bind to a first biological particle and a second binding moiety can bind to a second biological particle. The first binding moiety can bind to the second binding moiety to form the particle cluster. At least one of the first binding moiety and the second binding moiety can include an antibody or an antibody fragment. A first binding moiety can bind to a first biological particle, a second binding moiety can bind to a second biological particle, and at least a third binding moiety can bind the first binding moiety to the second binding moiety to form the particle cluster. At least one of the first binding moiety, the second binding moiety, and/or the third binding moiety can include an antibody or an antibody fragment.

In some implementations, the methods can further include cleaving the particle cluster when it reaches a predefined position in the microfluidic device such that the two or more particles making up the particle cluster are no longer bound to each other. Cleaving the particle cluster can include cleaving the particle cluster includes using at least one of light, an increase in temperature, a decrease in temperature, and/or a buffer composition.

The size-dependent force can include at least one of an inertial lift force and/or a deterministic lateral displacement force. The size-dependent force can include at least one of an acoustic force and/or a dielectric force.

In another aspect the present disclosure provides methods that include introducing a plurality of binding moieties into a fluid sample; allowing at least one of the binding moieties to bind two or more biological particles to form a particle cluster; and flowing the fluid sample comprising the particle cluster into a particle sorting region of a microfluidic device, wherein the particle sorting region divides the fluid sample into a first fluid stream within a first microfluidic channel and a second fluid stream within a second microfluidic channel, and wherein the particle cluster experiences a size-dependent force within the particle sorting region that is sufficient to drive the particle cluster into the first fluid stream and away from the second fluid stream; and cleaving the particle cluster when it reaches a predefined position in the microfluidic device such that the two or more cleaved particles making up the particle cluster are no longer bound to each other. The methods can further include introducing the fluid sample comprising the cleaved particle cluster into an additional particle sorting region, and sorting, within the additional particle sorting region, the two or more cleaved particles based on size.

Particle separation and filtration have been used in numerous applications across industries and fields. Examples of such applications include chemical process and fermentation filtration, water purification/waste water treatment, sorting and filtering components of blood, concentrating colloid solutions, and purifying and concentrating environmental samples. Various macro-scale techniques have been developed for use in these applications, including methods such as centrifugation and filter-based techniques. Typically, such techniques may require systems that are large, bulky, and expensive, and may have complex moving components.

The micro-scale techniques described herein offer advantages over macro-scale techniques, in that scaling down allows the use of unique hydrodynamic effects for particle sorting and filtration. Therefore, these techniques can eliminate the need for large systems with complex moving components. Moreover, micro-scale techniques offer the possibility of portable devices capable of performing sorting and filtration at lower cost than larger macro-scale systems.

As described herein, one can achieve fluidic forces that dominate on the microfluidic scale such that sorting and/or concentrating particles in a fluid sample based on size. Some techniques, for instance, use inertial lift force, which is a size-dependent fluidic force that acts on a particle. Inertial lift force arises due to a flow disturbances generated by the particle when the particle nears a wall in a microfluidic device, and can allow the separation/filtration of particles in a fluid sample based on size. Other techniques such as force driven deterministic lateral displacement also use size-dependent fluidic forces to separate particles in a fluid sample based on size. However, some microfluidic forces that are dependent on the size of the particles are generally not effective to separate similarly sized particles in a fluid sample. For example, it can be difficult to use microfluidic size-based sorting techniques to separate blood platelets from bacterial cells in a blood sample, as blood platelets and bacterial cells tend to be similar in size.

The present disclosure relates to methods and systems that seek to solve some or all of the aforementioned disadvantages. In particular, the methods disclosed herein include amplifying the size of particular particles such that they can be separated from other similarly-sized particles using size-based microfluidic sorting techniques. For example, in some implementations, one or more types of binding moieties are added to a fluid sample having at least bacteria, blood platelets, and red blood cells. The binding moieties act to bind the platelets with the red blood cells in the fluid sample to form particle clusters. The fluid sample is then allowed to flow through a particle sorting region of a microfluidic device, where the particle sorting region is configured to separate particles based on size by applying a size-dependent force to the particles of the fluid sample. As the fluid sample flows through the system, the smaller bacteria particles are separated from the larger particle clusters. Thus, the methods can be used to separate particles of similar size (e.g., platelets and bacteria cells) by using particle complexing techniques. At least one advantage of the present methods is that the present methods may provide techniques for separating particular biological particles from other similar sized particles. Another advantage of the present methods is that the methods may provide for a cost-effective approach for amplifying the size of particular biological particles compared to other amplification techniques, such as techniques that rely on introducing non-native particles to a fluid sample by, for example, introducing magnetic beads to form complexes. With the present techniques, particles that are naturally occurring within a fluid sample can be used to form complexes in place of particles that are artificially introduced into the fluid sample. This also has the added benefit of reduced reagent costs when compared to other techniques that rely on these artificially introduced particles.

For the purposes of the present disclosure, a binding moiety refers to a molecule, synthetic or natural, that specifically binds or otherwise links to, e.g., covalently or non-covalently binds to or hybridizes with, a target analyte, or with another binding moiety (or, in certain embodiments, with an aggregation inducing molecule). For example, a binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target analyte such as enzymes in solution. Binding moieties include, for example, oligonucleotides, polypeptides, antibodies, and polysaccharides. As an example, streptavidin (binding moiety) has four sites per molecule that will be recognized by biotin. For any given analyte, e.g., a specific type of cell, having a specific surface marker, there are typically many binding moieties that are known to those of skill in the relevant fields that can bind to the specific surface marker. For example, certain labeling methods and binding moiety techniques are discussed in detail in U.S. Pat. No. 6,540,896 entitled, "Microfabricated Cell Sorter for Chemical and Biological Materials" filed on May 21, 1999; U.S. Pat. No. 5,968,820 entitled, "Method for Magnetically Separating Cells into Fractionated Flow Streams" filed on Feb. 26, 1997; and U.S. Pat. No. 6,767,706 entitled, "Integrated Active Flux Microfluidic Devices and Methods" filed on Jun. 5, 2001, each of which is incorporated herein by reference in its entirety.

For the purposes of this disclosure, a biological particle refers to a mass of matter that naturally originates in living organisms. For example, a biological particle can be a biological molecule, cell, or collection of cells (e.g., red blood cell, white blood cell, blood platelet, cancer cells, among others), proteins, DNA, peptides, bacteria, archaea, fungi, protists, and so forth. A biological particle can include particles that are substantially biological in nature, which refers to a biological particle that includes a component that naturally originates in living organisms and that has been modified (e.g., genetically modified) to form a hybrid particle. For example, a living cell can be modified by the incorporation of one or more function-spacer-lipid constructs (FSL constructs) to produce kodecytes that exhibit novel biological, chemical, or technological functions. As another example, cells (e.g., red blood cells that have been stored in a blood bank) may be chemically fixated by, for instance, pre-labeling the cells with a complexing regent. As another example, cells can also be modified through one or more heat-kill processes. In some implementations, pre-labeling cells may include fluorescently pre-labeling the cells. In some implementations, cells can also be genetically engineered such that they express cell surface antigens not present on typical living cells. In some implementations, cells may be osmotically swelled or shrunk to change the effective size of the cell.

For the purposes of this disclosure, both a particle size and the effective size of a particle cluster correspond to a size associated with an equivalent shape having approximately the same property, such as the approximately same volume or the approximately same surface area, as the actual particle and particle cluster, respectively. For instance, the size of a particle may be expressed using a parameter such as the diameter, surface area, or volume of a sphere, where the sphere is an equivalent shape of the particle. Similarly, the effective size of a particle complex may also be expressed using a parameter such as the diameter, surface area, or volume of a sphere, where the sphere is an equivalent shape of the particle cluster (e.g. the equivalent sphere has a diameter which is about equal to the largest linear size of the cluster). As another example, the effective size of a particle/particle cluster may be expressed using a parameter such as the effective diameter of an ellipsoid, which can be the cube root of the product of all diameters of the ellipsoid, where the ellipsoid is an equivalent shape of the particle/particle cluster. Since not all particles and particle clusters are monodisperse in which each particle of a particular type has exactly the same dimensions or each particle cluster having the same component particles has exactly the same dimensions, the particle size and effective particle size may also represent an average size across a population of particles or particle clusters.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

BRIEF DESCRIPTION OF THE DRAWINGS

FIGS. 2A to 2C are illustrations showing methods for complexing particles, according to one or more embodiments of the present disclosure.

FIGS. 8A-8C are graphs and charts of experimental results showing the relative yields of red blood cells, platelets, and bacteria in the siphon and buffer outlets of a microfluidic device under various conditions.

FIGS. 9A-9C illustrate examples of experiments using techniques according to one or more embodiments of the present disclosure.

DETAILED DESCRIPTION

Figure 1:
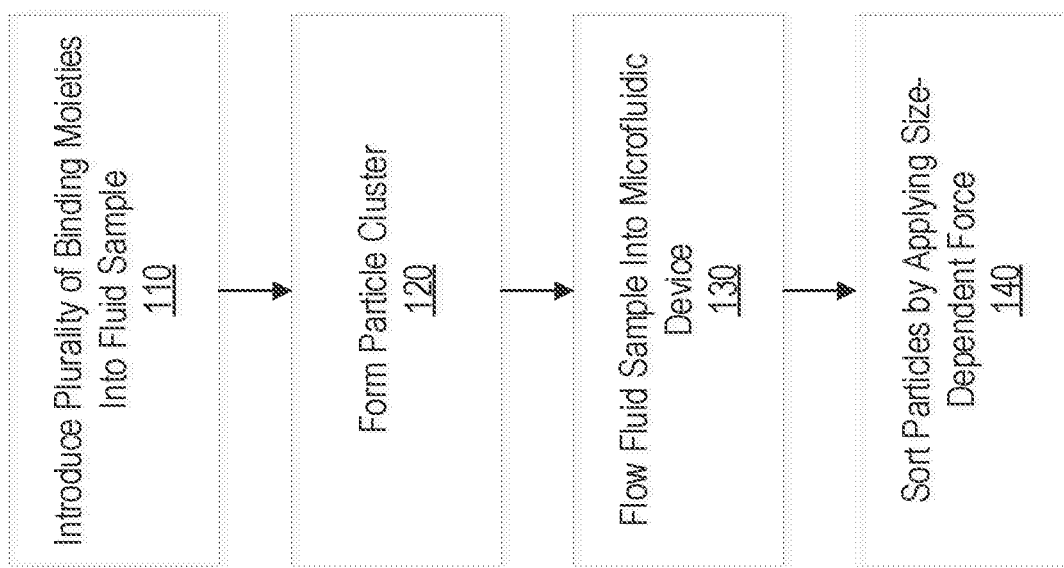
FIG. 1 is a flow chart showing an example of a method for size-based separation using particle size amplification via particle complexing.

For fluids confined to spaces measuring in the millimeter and sub-millimeter scales, certain behaviors of the fluids begin to have greater effect relative to forces that dominate in the macroscale. It is possible to leverage these behaviors, such as surface tension and fluidic resistance, to manipulate the fluid itself and, in some cases, particles within the fluids. An example of a force, for instance, that begins to dominate in microfluidic systems includes a forced referred to as "inertial lift." An inertial lift force is a size-dependent fluidic force that acts on a particle within a fluid sample, in which the force arises due to flow disturbances generated by the particle when the particle nears a wall in a microfluidic device. Particles that are larger in size will experience and be subject to a greater inertial lift force than smaller particles within the same fluid sample under the same fluidic conditions (e.g., fluid flow speed). Inertial lift forces therefore may be used in combination with particular microfluidic system designs to facilitate the size-based sorting of particles in a fluid sample. Further details on inertial lift forces in microfluidic systems and techniques for using inertial lift forces to manipulate particles within a fluid can be found, e.g., in U.S. Patent App. Pub. No. 2016/0121331, U.S. Patent App. Pub. No. 2016/0123858, U.S. Patent App. Pub. No. 2016/0123857, D. Di Carlo, D. Irimia, R. G. Tompkins, and M. Toner, "Continuous inertial focusing, ordering, and separation of particles in microchannels.," Proc. Natl. Acad. Sci. U.S.A., vol. 104, no. 48, pp. 18892-18897, November 2007; D. Di Carlo, J. F. Edd, K. J. Humphry, H. A. Stone, and M. Toner, "Particle segregation and dynamics in confined flows," Phys. Rev. Lett., vol. 102, no. 9, p. 094503, March 2009; and D. Di Carlo, "Inertial microfluidics," Lab Chip, vol. 9, no. 21, p. 3038, 2009, each of which is incorporated herein by reference in its entirety.

Other size-dependent microfluidic techniques for manipulating particles within fluids include, e.g., deterministic lateral displacement, acoustic focusing, viscoelastic focusing, and dielectrophoresis, among others. Further details on such forces may be found, e.g., in J. McGrath, M. Jiminez, and H. Bridle, "Deterministic lateral displacement for particle separation: a review;" T. Laurell, F. Petersson, and A. Nilsson, "Chip integrated strategies for acoustic separation and manipulation of cells and particles;" M. Li, W. Li, J. Zhang, G. Alici, and W. Wen, "A review of microfabrication techniques and dielectrophoretic microdevices for particle manipulation and separation;" each of which is incorporated herein by reference in its entirety. However, because the foregoing forces are dependent on the particle size, these techniques are generally not effective to separate similar sized particles in a fluid sample. For example, it can be difficult to use particle size-based forces to separate blood platelets from bacterial cells in a blood sample, as blood platelets and bacterial cells tend to be similar in size. As explained herein, techniques for amplifying the size of particles can be used with size-based microfluidic sorting devices to provide highly efficient particle sorting and/or concentrating devices.

Method Overview

FIG. 1 is a flow chart showing an example of a method for size-based sorting within microfluidic devices using particle size amplification via particle complexing, according to one or more embodiments of the present disclosure. The method includes introducing multiple binding moieties into a fluid sample (block 110), allowing the binding moieties to bind particles within the fluid sample together to form one or more particle clusters (block 120), flowing the fluid sample that includes the one or more particle clusters into a particle separation stage of a microfluidic device (block 130), and sorting particles by applying a size-dependent force to the particles (block 140).

At block 110, multiple binding moieties are introduced into a fluid sample. The fluid sample may include one or more types of biological particles to which the binding moieties can bind to allow the formation of particle clusters as explained herein. The multiple binding moieties can include a single type of binding moiety or multiple different types of binding moieties. In some implementations, the multiple binding moieties include at least one antibody directed toward an antigen or any protein-protein interaction. The multiple binding moieties can include binding moieties designed or selected to serve, when bound to another binding moiety, as substrates for a target molecule such as an enzyme in a solution. In some implementations, the multiple binding moieties include one or more recombinant proteins, one or more polymers, one or more antibody fragments, one or more aptamers, one or more polysaccharides, one or more biotinylated antibodies, and/or one or more tetrameric antibody complexes. The multiple binding moieties can include at least one synthetic molecule such as, for example, a synthetic oligonucleotide that hybridizes to a specific complementary nucleic acid target.

The binding moieties can target particular biological particles for binding. For example, in an embodiment, the multiple binding moieties include binding moieties that target anti-human CD41 and/or CD61 antigens expressed by blood platelets and/or binding moieties that target anti-human CD235a antigens expressed on red blood cells. Consequently, the binding moieties can be chosen and/or designed to bind to certain biological particles of interest without binding to other biological particles that may be present in the fluid sample. The multiple binding moieties can also include binding moieties that target other binding moieties. For example, in an embodiment, the multiple binding moieties include anti-mouse IgG Fc antibodies to bind to the Fc domains of anti-human CD41 and anti-human CD235a antibodies. Therefore, the multiple binding moieties can include binding moieties that target certain biological particles along with binding moieties that bind together the binding moieties that target certain biological particles.

In an embodiment, the fluid sample is a bodily fluid, including, but not limited to, blood, urine, amniotic fluid, bile, blood plasma, or cerebrospinal fluid. In an embodiment, the fluid sample is a diluted bodily fluid (e.g., diluted blood or diluted urine). In an embodiment, the fluid sample includes one or more saline solutions, a lysis buffer, or an anticoagulant, such as Ethylenediaminetetraacetic acid (EDTA), among other fluids. As explained herein, the fluid sample may include multiple biological particles. The biological particles may naturally occur within the fluid sample. For instance, the fluid sample may include blood and the particles may include blood cells. The multiple biological particles may include multiple different types of biological particles. For example, in some implementations, the biological particles in the fluid sample include multiple different blood cells, such as red blood cells, white blood cells and/or blood platelets. Alternatively or in addition, the fluid sample includes bacteria cells, cancer cells, proteins, DNA, RNA, peptides, archaea, fungi, or protists, among other types of particles. The biological particles may include particles that are substantially biological in nature. In some implementations, the biological particles are added to the fluid sample, including before or after the binding moieties are introduced into the fluid sample. For example, red blood cells and/or blood platelets can be added to the fluid sample after binding moieties are introduced into the fluid sample.

At block 102, the multiple binding moieties are allowed to bind two or more biological particles within the fluid sample to form a particle cluster. The two or more particles can be the same type of biological particles, different types of biological particles, or a combination of different types and the same types of biological particles. As an example, a particle cluster can be formed that includes a red blood cell bound to a blood platelet through one or more types of binding moieties. As another example, a particle cluster can be formed in which the one or more binding moieties bind together two or more blood platelets. In another example, a particle cluster can be formed in which the bonding moieties bind two platelets to a single red blood cell.

By allowing the binding moieties to bind together particles of different types and/or of the same types, it is possible to create a particle complex having a larger effective size than the size of the individual particles that make up the particle complex. Both a particle size and the effective size of a particle cluster correspond to a size associated with an equivalent shape having approximately the same property, such as the approximately same volume or the approximately same surface area, as the actual particle and particle cluster, respectively. For instance, the size of a particle may be expressed using a parameter such as the diameter, surface area, or volume of a sphere, where the sphere is an equivalent shape of the particle. Similarly, the effective size of a particle complex may also be expressed using a parameter such as the diameter, surface area, or volume of a sphere, where the sphere is an equivalent shape of the particle cluster. Since not all particles and particle clusters are monodisperse in which each particle of a particular type has exactly the same dimensions or each particle cluster having the same component particles has exactly the same dimensions, the particle size and effective particle size may also represent an average size across a population of particles or particle clusters.

In some implementations, the fluid sample including the biological particles and binding moieties is incubated for a predetermined interval of time to facilitate particle complexing. The fluid sample can also be incubated more than once, where each incubation cycle consist of a predetermined interval of time. For example, the predetermined period of time can include 1 minutes, 10 minutes, 20 minutes, 30 minutes, 1 hour, 2 hours, 5 hours, 12 hours, or 24 hours, among other predetermined intervals of time depending on the amount of time needed to allow binding moieties to bind to biological particles within the fluid sample. In an embodiment, the fluid sample is incubated twice, each incubation cycle being an hour in length. As previously indicated, the binding moieties can be added to a fluid sample that is substantially free of biological particles. In an embodiment, multiple biological particles of a first type (e.g., erythrocytes) are added to a fluid sample after the multiple binding moieties are introduced in the fluid sample (e.g., mouse IgG monoclonal antibodies) and then incubated for an hour. In some implementations, multiple biological particles of a second type (e.g., leukocytes) are added to the fluid sample (e.g., the complex solution of binding moieties and biological particles of the first type) and incubated for another hour. In an embodiment, the fluid sample includes one or more biotin-binding proteins, such as Avidin, streptavidin, and/or neutravidin.

In some implementations, the biological particles included within the fluid sample have a relative ratio such that aggregation of the particles can be driven to a point where it stops due to substantially full coverage of at least one biological particle (e.g., where the at least one biological particle is bound to so many other particles of a different type, there is no room on the at least one biological particle to bind to any further particles of the different type). For example, with RBCs and platelets, a natural endpoint is a single platelet completely covered by RBCs (e.g., two RBCs stacked side to side with a bridging platelet). Because, in some instances, RBCs may outnumber platelets 10:1 in the fluid sample, this endpoint can prevent larger aggregates from forming. This may be beneficial for microfluidic size based sorting since limiting aggregation can avoid clog-inducing aggregates that may be too large to traverse through the channels of a microfluidic device. In some implementations, ratio of concentration of a first type of particle to a concentration of a second type of particle within a microfluidic sample that may drive aggregation to such endpoints include, for example, 10:1, 20:1, 50:1, 100:1, or 1000:1. Other ratios are also possible.

As previously indicated, the binding moieties can target specific biological particles for binding to form one or more particle clusters. The one or more particle clusters can be formed by several combinations of binding moieties and biological particles. For example, in some implementations, one or more particle clusters are formed as a first binding moiety binds to a first biological particle of a first type (e.g., a white blood cell), and a second binding moiety binds to a second biological particle of a second type that is different than the first type (e.g., a platelet), and the first binding moiety binds to the second binding moiety. In some implementations, one or more particle clusters are formed as a first binding moiety binds to a first biological particle of a first type (e.g., a red blood cell), a second binding moiety binds to a second biological particle of a second type that is different from the first type (e.g., a platelet), and at least a third binding moiety binds the first binding moiety to the second binding moiety to form a particle cluster. In an embodiment, a binding moiety includes two or more binding sites, each binding site targeting at least one specific biological particle of a particular type.

For example, FIGS. 2A-2C are illustrations showing examples of particle clusters, according to one or more embodiments of the present disclosure. As FIGS. 2A-2C show, the particle clusters can have an effective size larger than the effective size of the individual particles that form the particle clusters. Referring to FIG. 2A, three binding moieties are used to bind a first biological particle 210 to a second biological particle 220. For the purposes of this example, the binding moieties will be understood to form a tetrameric antibody complex. In the shown embodiment, the first biological particle 210 may include a red blood cell 210, and the second biological particle 220 may include a blood platelet 220. The tetrameric antibody complex includes a first binding moiety 211, a second binding moiety 221, and a third binding moiety 231. As shown in the example of FIG. 2A, a first end of the first binding moiety 211 is bound to a first end of the third binding moiety 231. A first end of the second binding moiety 221 is bound to a second end of the third binding moiety 231. A second end of the first binding moiety 211 targets an antigen on the first biological particle 210. For instance, the second end of the first binding moiety 211 may include an anti-human CD 235$a$ IgG2 antibody that targets the human CD235a (i.e., the glycophorin A sialoglycoprotein expressed on red blood cell membranes) antigen on the red blood cell's 210 surface. The second end of the second binding moiety 231 targets an antigen on the second biological particle 220. For instance, the second binding moiety 221 may include an anti-human CD41 igG antibody that targets the CD41 antigen on the surface of the platelet 220. The third binding moiety 231 may include, e.g., a Goat F(ab') anti-mouse IgG Fc antibody that binds to the Fc domains (i.e., fragment crystallizable domain) of the anti-human CD235a and anti-human CD41 antibodies (i.e., first binding moiety 211 and second binding moiety 221 respectively). Thus, a particle cluster can be formed by using three binding moieties, where one binding moiety binds to a first type of particle, a second binding moiety binds to a second type of particle, and a third binding moiety binds the first and second binding moieties together.

FIG. 2B is a schematic that illustrates another example of a particle cluster. Referring to FIG. 2B, a particle cluster can be formed by binding two or more of the same types of binding moieties 251 to a binding protein 241 at one end of the binding moieties 251 and binding a biological particle 250 at a second end of each binding moiety 251. In the shown embodiment, the binding protein 241 is a biotin binding protein 241 that binds to the four binding moieties 251, which are biotinylated antibodies. Each of the four binding moieties 251 has a biological particle 250 (e.g., platelet 250) attached. The biotin binding protein 241 is Avidin, which has four biotin binding sites. The biotinylated antibodies 251 are Anti-human CD41 IgG antibodies with biotin covalently attached to an end. Thus, a particle cluster having four platelets 250 is formed by exploiting Avidin's four biotin binding sites to bind four biotinylated antibodies having platelets 250 attached to an end.

FIG. 2C is a schematic that illustrates another example of a particle cluster. Referring to FIG. 2C, a first biological particle 260 is bound to one end of a first binding moiety 261 and a second biological particle 270 is bound to one end of a second binding moiety 271. The first binding moiety 261 and the second binding moiety 271 are bound together via a chemical process. For instance, particle cluster can be formed by exchanging the CH1 domain of one heavy chain (e.g., large polypeptide subunit of an antibody) of the first antibody 261 with the constant domain of the corresponding light chain (e.g., small polypeptide subunit of an antibody) of the second antibody 271 to pair the light chains of the two antibodies 261, 271. In the shown embodiment, the first antibody 261 is an anti-human CD 235a IgG2 antibody and the second antibody 271 is an anti-human CD41 igG antibody. The first biological particle 260 is a red blood cell and the second biological particle 270 is a blood platelet.

Referring back to FIG. 1, at block 130 the sample fluid, which includes one or more formed particle clusters, such as the particle clusters described herein, is sent through a particle sorting region of a microfluidic device. In an embodiment, the particle sorting region is configured to apply a size-dependent force to the particles of the fluid sample (e.g., the biological particles and the particle cluster). The particle sorting region can be configured to divide the fluid sample into a first fluid stream within a first microfluidic channel and a second fluid stream within a second microfluidic channel.

At block 140, the particles of the fluid sample experience a size-dependent force within the particle sorting region of the microfluidic device. In some implementations, the one or more particle clusters experience a size-dependent force within the particle sorting and/or concentrating region that is sufficient to drive the particle cluster into the first fluid stream and away from the second fluid stream. The particle sorting regions of the microfluidic device can include walls that impart an inertial lift force, or other size-dependent fluidic forces, to drive the one or more particle clusters away from the second fluid stream. Examples of microfluidic devices that utilizes inertial lift forces is further detailed below with reference to FIGS. 3-7.

In some implementations, the microfluidic device uses a technique referred to as deterministic lateral displacement to separate and/or filter the particle clusters in the fluid sample. Deterministic lateral displacement describes a size-based particle separation/filtration technique in which posts (or other physical structures) within a channel are specifically arranged to precisely control the trajectory of and facilitate separation of particles larger and smaller than a critical diameter via a size-dependent bumping force from direct contact of the particles with the posts. Alternatively, or in addition, the microfluidic device uses acoustic focusing, viscoelastic focusing, dielectrophoresis, and/or other size-dependent particle sorting techniques to facilitate the sorting of particles, to include the one or more particle clusters, in the fluid sample by size.

As previously indicated, the fluid sample can include more than one type of biological particle. In an embodiment, the fluid sample includes a first type of biological particle, a second type of biological particle and a third type of biological particle, where the first type and second type of biological particle forms the one or more particle clusters. In some implementations, the average size of the first type of substantially biological particle is larger than the average size of the second type of biological particle. For example, the first type of biological particle may have a larger average diameter, larger average surface area, or larger average volume than an average diameter, average surface area, or average volume, respectively of the second type of biological particle. In an embodiment, the average size of the third type of biological particle is substantially equal to an average size of the first and/or second type of biological particles (or their size distributions at least partially overlap). In some implementations, the average size of the third type of biological particle is smaller than the average size of the particle cluster. For example, the fluid sample can include blood (e.g., either whole blood or diluted blood), in which the first type of particle is a red blood cell (or white blood cell), the second type of particle is a blood platelet, and the third type of particle is a bacteria cell. In this instance, the average size of the blood platelet and bacteria cells are approximately equal (or their size distributions overlap). In an embodiment, the platelets are bound to the red blood cells through one or more binding moieties, as explained herein, to form the one or more particle clusters. Thus, the fluid sample can include blood (either whole or diluted) having red blood cells, platelets, red blood cell-platelet particle clusters, and bacteria cells.

As previously indicated, the particle sorting region of the microfluidic device can divide the fluid sample into a first fluid stream and a second fluid stream. In an embodiment, the third type of biological particles (e.g., bacteria cells) in the fluid sample flows with the portion of the fluid sample from the first microfluidic channel (e.g., from the first stream) into the second microfluidic channels (e.g., into the second stream). For example, because the particle sorting region uses size-dependent forces to separate particles, the larger particles (e.g., red blood cells) and particle clusters (e.g., red blood cell-platelet cluster) can experience size-dependent forces sufficient enough to keep them in the first fluid stream, while the smaller particles (e.g., platelets) do not experience enough force to keep them in the first fluid stream. Thus, the smaller particles can be separated from the larger particles. In some implementations, the microfluidic device includes more particle sorting regions configured to separate the particle clusters from the other particle types (e.g., separating particle clusters from other red blood cells and/or white blood cells).

In some implementations, the particle sorting region of the microfluidic device includes a third microfluidic channel, as discussed below with reference to FIG. 7. A second fluid sample can be processed through the third microfluidic channel. Additionally, at least a portion of the second fluid sample can flow from the third microfluidic channel into the first microfluidic channel. In some implementations, the particle cluster experiences a size-dependent force sufficient enough to drive the particle cluster from the first fluid sample into the portion of the second fluid sample. In some implementations, the second fluid sample is a buffer solution. In some implementations, at least one of the binding moieties is cleavable (e.g., using ultraviolet energy, lyases, and/or other cleaving agents, or by an increase in temperature, a decrease in temperature, or by a buffer composition). Thus, after being separated from the other smaller particles, the particle clusters formed from the binding moieties can be cleaved by splitting the chemical bonds holding the particles and binding moieties together. The particle clusters can be cleaved at a predefined position in the microfluidic device. For instance, the particle clusters can be cleaved within the particle sorting region or in a section of the microfluidic device downstream of the particle sorting region. In some implementations, the cleaved particles are also separated by size after being cleaved. The separation of the cleaved particles may be achieved in an additional particle sorting region within the microfluidic device. The separation of the cleaved particles can be accomplished using size-dependent forces, such as those discussed herein, or using other techniques that are not necessarily dependent on the size of the particles being separated. For example, once the aforementioned red blood cell-platelet clusters are separated from the bacteria cells in the blood fluid sample, the red blood cell-platelet clusters can be cleaved into individual red blood cells and platelets using ultraviolet radiation. Then the red blood cells and platelets can be separated from one another using any one of the aforementioned size-dependent sorting techniques.

Examples of Microfluidic Devices

Figure 3:
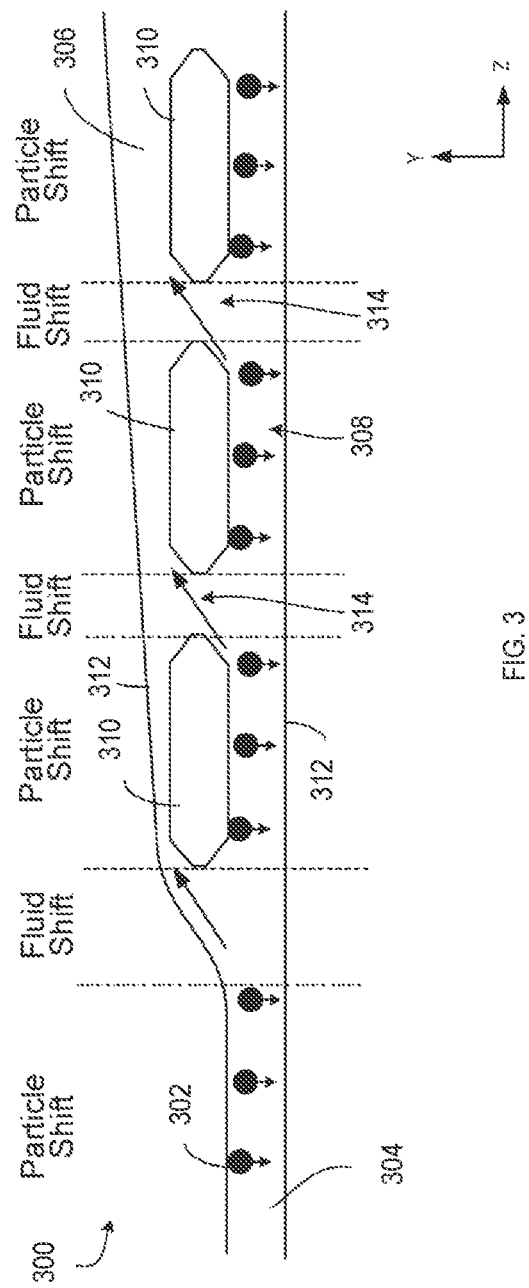
FIG. 3 is a schematic that illustrates a top view of an example of a microfluidic device capable of shifting the position of particles across fluid streamlines while the fluid propagates through the microfluidic device, according to one or more embodiments of the present disclosure.

FIG. 3 is a schematic that illustrates a top view of an example of a microfluidic device 300 capable of shifting the position of particles 302 across fluid streamlines while the fluid propagates through the microfluidic device 300. As will be explained, the particle shifting across fluid streamlines relies on the inertial lift forces experienced by particles as fluid is periodically extracted from a microfluidic channel, though other repulsive forces, and even attractive forces, may be used in place of or in addition to inertial lift forces. For reference, a Cartesian coordinate system is shown, in which the x-direction extends into and out of the page.

During operation of the device 300, a fluid carrying the particles 302 is introduced through an inlet microfluidic channel 304. In some implementations, the particles 302 include the particle clusters formed in block 120, as discussed earlier with reference to FIG. 1. In this and other implementations of the particle shifting devices, the fluid can be introduced through the use of a pump or other fluid actuation mechanism. The inlet channel 304 splits into two different fluid flow channels (second micro fluidic channel 306 and first micro fluidic channel 308 substantially parallel to the second micro fluidic channel 306) that are separated by a 1-dimensional array of rigid island structures 310. The 1-dimensional array of island structures 310 extends substantially in the same direction as the flow of the fluid through the second and first micro fluidic channels. Each island structure 310 in the array is separated from an adjacent island 310 by an opening or gap 314 through which fluid can flow. Each gap 314 in the example of FIG. 3 has the same distance between adjacent islands 310. In other implementations, different gaps can have different distances between adjacent islands 310. For example, in some implementations, a length of each subsequent opening (e.g., as measured along the fluid propagation direction—the z-direction in FIG. 3) in the first array is greater than a size of a previous opening in the array. Furthermore, although a 1-dimensional array is shown in FIG. 3, the islands 310 may be arranged in different configurations including, for example, a two-dimensional array of islands. The boundaries of the fluid flow regions within the microfluidic channels are defined by the device walls 312 and the walls of the islands 310.

As the fluid propagates substantially along the z-direction (i.e., the longitudinal direction) from the inlet channel 304 to the channels (306, 308), particles 302 experience a force (in this example, an inertial lift force) that causes the particles 302 to shift across fluid streamlines and travel along the first microfluidic channel 308. These inertial lift forces are in the negative y-direction (see short arrows adjacent to each particle 302 in FIG. 3).

For instance, when a particle 302 is located in the inlet channel 304 and approaches the top wall 312, the particle 302 experiences an inertial lift force that pushes the particle 302 down toward the first microfluidic channel 308. Once in the first microfluidic channel 308, the particle 302 may approach a wall of the first island 310, such that it again experiences an inertial lift force pushing the particle 302 down, maintaining the particle 302 within the first microfluidic channel 308. The repeated application of the inertial lift force to the particle 302 in each of the "particle shift" regions shown in FIG. 3 thus serves to separate/filter the particle from the fluid propagating through the second microfluidic channel 306. At the same time, portions of the fluid traveling in the first microfluidic channel 308 are extracted (e.g., siphoned)/pass into the second microfluidic channel at one or more "fluid shift" regions (see FIG. 3) in the device 300.

In the example of FIG. 3, each fluid shift region corresponds to an opening or gap that extends between the first microfluidic channel 308 and the second microfluidic channel 306. Each "fluid shift" region primarily allows fluid to be extracted from the first microfluidic channel 308 into the second microfluidic channel 306. The movement of fluid into the gaps tends to pull the particles 302 toward the gaps as well, since the particles follow the fluid streamlines. However, as the particles move closer to the gaps 314, they approach the island structures 312, which impart an inertial lift force causing the incident particles to cross fluid streamlines in a direction away from the gaps 314. That is, the particles 302 shift from a fluid streamline passing into the second microfluidic channel 306 to a fluid streamline that continues to flow in the first microfluidic channel 308. As a result, the particles 302 continue to propagate in the first microfluidic channel 308 and are not shifted into the second microfluidic channel 306 with the fluid. If there were no fluid shifting from the first microfluidic channel 308 to the second microfluidic channel 306, the particles would migrate as a result of inertial focusing toward equilibrium focusing positions where the inertial lift force and shear gradient force are balanced. However, by shifting the fluid across the channels, the particles 302 tend to follow the fluid toward areas where the inertial lift force is much stronger than the shear gradient force, thus causing the particles to shift across streamlines in a very efficient and controlled manner.

In the present example, the fluid is extracted through the fluid shift regions as a result of decrease in fluidic resistance along a longitudinal section of the fluid shift region. That is, for a fluid of constant viscosity, the gaps 314 between adjacent islands 310 increase the channel area through which the fluid can flow, resulting in a reduced fluidic resistance. As fluid propagates through the device 300 and arrives at a gap 314, a portion of the fluid will flow into the gap 314 and subsequently into the second microfluidic channel 306 (i.e., the fluid portion is extracted into channel 306). The decrease in fluidic resistance also can occur as a result of the increasing channel width in the second microfluidic channel 306. In particular, the second microfluidic channel wall 312 is slanted at an angle away from the islands so that the width of the second microfluidic channel 306 increases along the channel's longitudinal direction (i.e., in the direction of fluid propagation or the positive z-direction), thus causing a decrease in fluidic resistance. Any increase in the cross-sectional area of the channel 306 along the longitudinal direction of the first microfluidic channel, not just an increase in width, also can be employed to reduce the fluidic resistance.

Alternatively, or in addition, the fluid may experience an increase in fluidic resistance in channel 308 relative to the fluidic resistance of channel 306 (e.g., through a decrease in the cross-sectional area of the channel 308 along the longitudinal direction). Thus, it may be said that the fluid is extracted in response to a change in the relative fluidic resistance between the second and first microfluidic channels. The change in the relative fluidic resistance may occur over the entire particle sorting region or over a portion of the sorting region that is less than the entire particle sorting region. The change in the relative fluidic resistance may occur over along the direction of the fluid flow through the particle sorting region (e.g., along a longitudinal direction of the particle sorting region as shown in FIG. 3).

With progressively lower fluidic resistance at the gaps 314 and/or in channel 306, greater amounts of fluid flow into the second microfluidic channel 306. Furthermore, the repeated shifting of fluid into the second channel 306 reduces the amount of fluid in the first channel 308. This constant fluid extraction thus increases the particle-to-fluid concentration in the first channel 308, while decreasing the concentration of particles in the second microfluidic channel 306, such that the fluid in the second microfluidic channel 306 is "filtered" or "purified." In some implementations, the particle shifting techniques disclosed herein may be capable of increasing the particle concentration from an initial fluid sample by up to 10, 25, 50, 75, 100, 200, 300, 400, or 500 times the initial particle to fluid concentration. Such concentration increases can result in particle yields from fluid samples of up to 90%, up to 95%, up to 99% or even 100%.

In some implementations, the increases in particle concentrations may be achieved using multiple microfluidic devices configured to employ the particle shifting techniques disclosed herein. For example, the output of a first microfluidic device configured to increase the particle concentration of an incoming fluid sample by 10× may be coupled to an input of a second microfluidic device configured to increase the particle concentration of an incoming fluid sample by 50×, for an overall increase in particles concentration from the initial fluid sample of 500×.

In addition to increasing particle concentration, the repeated particle shifting may also be used to focus the particles along one or more desired positions/streamlines within the fluid propagating through the lower channel 308. For instance, portions of fluid may be extracted from an initial microfluidic channel into one or more parallel microfluidic channels. In some instances, the parallel microfluidic channels containing the extracted fluid then may be recombined with the initial microfluidic channel downstream so that the particles are confined to designated streamlines in a single channel. An advantage of this technique of combining fluid shifting with inertial lift force is that particles may be focused to desired positions within the downstream channel (e.g., near the channel wall, at the middle of the channel, or halfway between the channel wall and the middle of the channel, among other positions) by controlling how much fluid is removed from each side of the initial channel, providing increased flexibility to the design and use of microfluidic devices. In contrast, for microfluidic systems based primarily on inertial focusing, one cannot choose the position of the focused stream within the channel.

The resulting concentrated and focused particle streamline may be coupled to a separate processing region of the microfluidic device 300 or removed from the device 300 for additional processing and/or analysis. Likewise, the "filtered" fluid in the second channel 306 may be coupled to a separate region of the microfluidic device 300 or removed from the device 300 for additional processing and/or analysis. In some implementations, the particles 302 entering the device 300 are "pre-focused" to a desired fluid streamline position that is aligned with the first microfluidic channel 308. By pre-focusing the particles 302 to a desired position, the probability that particles inadvertently enter into the second microfluidic channel 306 can be reduced.

Figure 4:
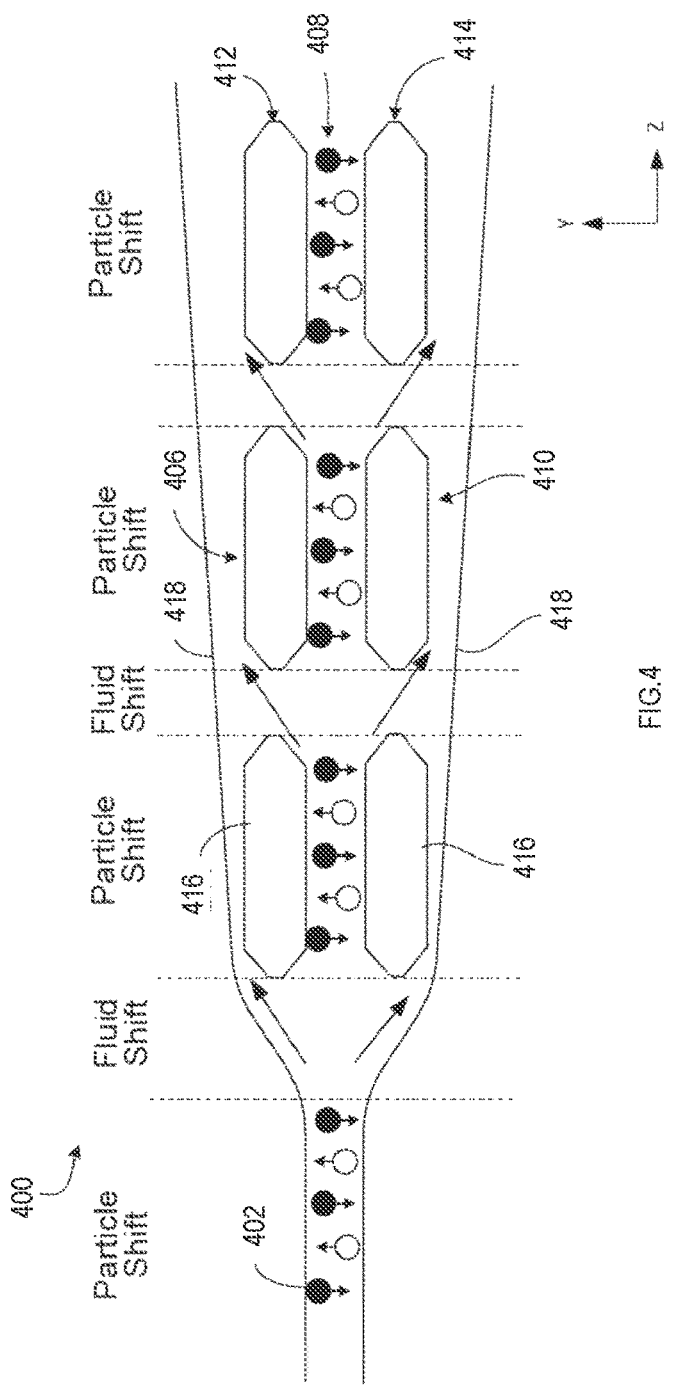
FIG. 4 is a schematic that illustrates an example of a device for particle and fluid shifting, in which the particle shifting area includes two different microfluidic channels for extracting fluid, rather than one microfluidic channel, according to one or more embodiments of the present disclosure.

For example, FIG. 4 is a schematic that illustrates an example of a device 400 for particle and fluid shifting, in which the particle shifting area includes two different microfluidic channels for extracting fluid, rather than one microfluidic channel, according to one or more embodiments of the present disclosure. The device 400 includes an inlet microfluidic channel 404 that is fluidly coupled to a particle shifting region that has three different fluid flow regions (an second microfluidic channel 406, a first microfluidic channel 408, and a third microfluidic channel 410). The second microfluidic channel 406 is separated from the first microfluidic channel 408 by a first array 412 of islands 416. The third microfluidic channel 410 is separated from the first microfluidic channel 408 by a second array 414 of islands 416. Each adjacent island in the first array 412 and each adjacent island in the second array 414 is separated by a gap for fluid shifting. The boundaries of the microfluidic channels 406, 408 are defined by the device walls 418 and the walls of the islands. The microfluidic channel walls 418 are slanted at angles away from the islands so that the widths of the second and third microfluidic channels (406, 410) increase along the fluid propagation direction (i.e., the positive z-direction), thus causing a decrease in fluidic resistance in each channel.

The device 400 operates in a similar manner to the device 300 discussed previously with reference to FIG. 3. In particular, as fluid propagates substantially along the z-direction from the inlet channel 404 to the channels (406, 408, 410), particles 402 within the fluid experience inertial lift forces in the "particle shift" regions upon approaching the walls of the inlet channel 404 and the walls of the island structures 416. In some implementations, the particles 402 include the particle clusters formed in block 120 discussed previously with reference to FIG. 1. The inertial lift forces in the inlet channel 404 push the particles 402 toward the center of the fluid flow (i.e., the inertial lift forces "focus" the particles toward central fluid streamlines), such that they primarily flow into the first microfluidic channel 408. Once the particles 402 enter the first microfluidic channel 408, they experience inertial lift forces from the island structures 416 that continue to focus the particles 402 along one or more central streamlines extending through the channel 408. At the same time, fluid is extracted into the second and third microfluidic channels (406, 410) in the "fluid shift" regions due to the reduced fluidic resistance. The combination of the fluid shift regions and the particle shift regions serve to focus particles from the incoming fluid into the first channel 408, while increasing the concentration of the particles at the same time. Any of the resulting fluid streams (from the second, first, or third channels) may be coupled to a separate region of the microfluidic device 400 or removed from the device 400 for additional processing or analysis. In some implementations, the variation in size/fluidic resistance of the second and third channels can be set so as to ensure that equal amounts of fluid flow in from the third channel and out the second channel at each unit.

Figure 5:
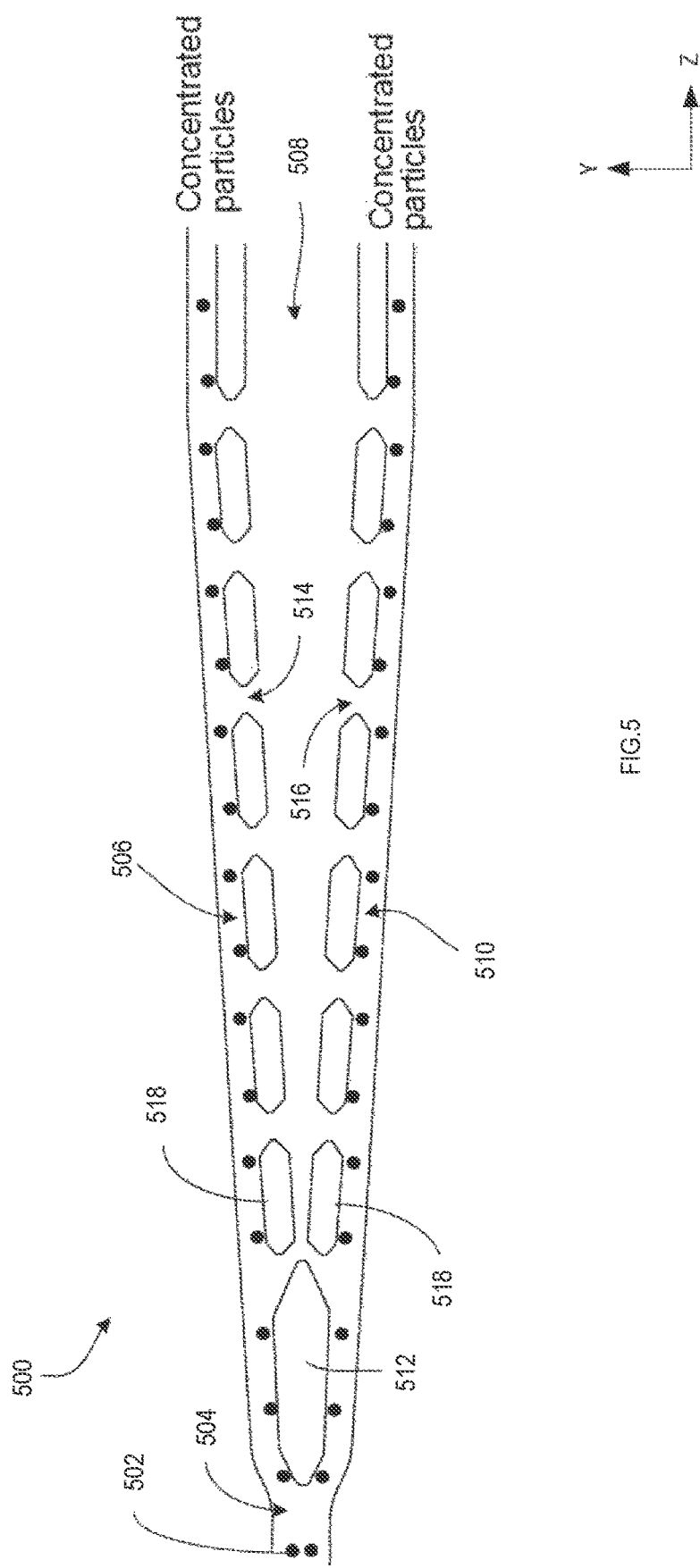
FIG. 5 is a schematic of a device 500 in which particle shifting concentrates particles from one stream along two different micro fluidic channels, according to one or more embodiments of the present disclosure.

In some cases, particle and fluid shifting can be used to create multiple different streams of focused/concentrated particles. For instance, FIG. 5 is a schematic of a device 500 in which particle shifting concentrates particles from one stream along two different micro fluidic channels, according to one or more embodiments of the present disclosure. The device 500 includes an inlet micro fluidic channel 504 that is fluidly coupled to two different fluid flow regions (a second micro fluidic channel 506 and a third micro fluidic channel 510). A single island structure 512 positioned at the coupling point between the inlet channel 404 and the second and third channels (506, 510) splits fluid propagating from the inlet channel 504 into two streams: one propagating along the second channel 506 and one propagating along the third channel 510. Downstream from the first island structure 512, the second microfluidic channel 506 is separated from the third microfluidic channel 510 by both a first array 514 of islands 518 and a second array 516 of islands 518. Each adjacent island in the first array 514 and each adjacent island in the second array 516 is separated by a gap for fluid shifting.

During operation of the device 500, a fluid containing particles 502 enters from the inlet channel 504. In an embodiment, the particles 502 include the one or more particle clusters formed in block 120 as discussed earlier with reference to FIG. 1. The fluid is separated by island 512 causing the fluid and the particles within the fluid to flow into either the second microfluidic channel 506 or the third microfluidic channel 510. Once the particles 502 have entered the second and third channels (506, 510), the particles remain concentrated within those channels due to repeated particle shifting (e.g., as a result of inertial lift forces) that occurs when the particles 502 approach the islands 518. A first microfluidic channel 508 is used to repeatedly extract fluid from the second and third channels (506, 510). In particular, the first channel 508 progressively increases in width, resulting in a lower fluidic resistance. Fluid is extracted from the second and third channels (506, 510) at the gaps between the islands 518 and follows this path of lower resistance. The device 500 thus takes a fluid containing randomly distributed particles and focuses/concentrates those particles into two separate streamlines in the second and third microfluidic channels 506, 510. The resulting particle streamlines and may be coupled to separate outputs for additional processing or analysis. The particle and shifting techniques described herein also may be used to shift particles from a first fluid to a second different fluid, where the concentration of the particles in the second fluid can be increased.

Figure 6:
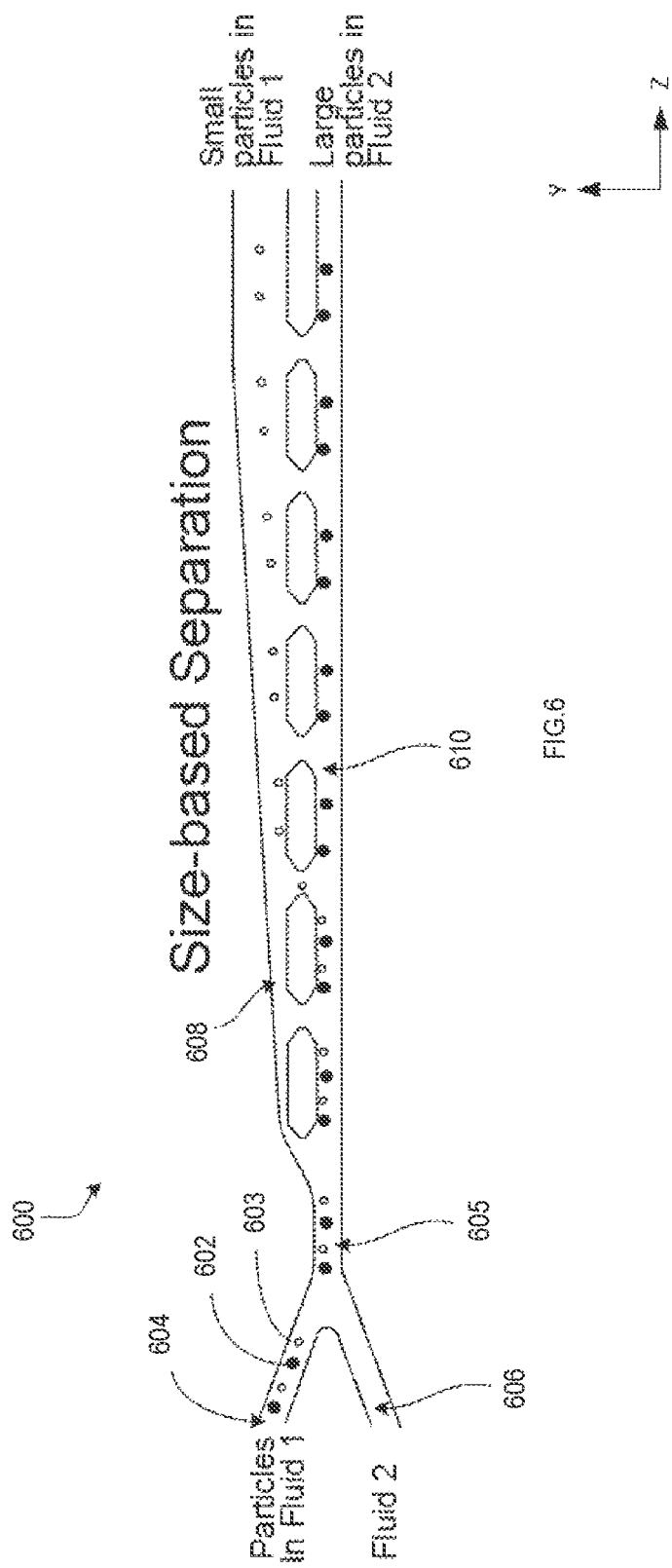
FIG. 6 is a schematic that illustrates an example of a device 600 being used for size-based sorting of particles, according to one or more embodiments of the present disclosure.

FIG. 6 is a schematic that illustrates an example of a device 600 being used for size-based sorting of particles, according to one or more embodiments of the present disclosure. During operation of the device 600, a first fluid ("Fluid 1") containing particles of different sizes (large particles 602 and small particles 603) is introduced into in the first inlet channel 604, and a second fluid ("Fluid 2") having no particles is introduced into the second inlet channel 606. In some implementations, the large particles 602 are the one or more clusters formed in block 120 (e.g., the first and second type of particles bound together using the binding moieties), as discussed earlier with reference to FIG. 1. In some implementations, the small particles are the third type of particles (e.g., platelets) discussed in block 130 with reference to FIG. 1. The first and second fluids may be the same type or different types of fluids. Again, assuming the fluids are introduced at flow rates corresponding to low Reynolds numbers (and thus laminar flow), there is little mixing between the two different fluids in the merge region 605, i.e., the two fluids essentially continue flowing as layers adjacent to one another. As the two fluids enter the first microfluidic channel 610, the forces on the larger particles 602 are great enough to keep the particles 602 within the first microfluidic channel 610. In contrast, the forces on the smaller particles 603 are not high enough to prevent the small particles 603 from being extracted with the first fluid into the second microfluidic channel 608. After repeated particle shifting and fluid extraction over a sufficient distance, most of the first fluid and the small particles 603 are extracted into the second channel 608, whereas the large particles 602 and most of the second fluid remain in the first channel 610. This process, also called fractionation, is useful for separating particles from a fluid based on size.

There are multiple reasons why large particles 602 are preferentially retained over the smaller particles 603. First, the inertial lift force is highly nonlinear in particle diameter. For instance, it is believed that near channel walls, the inertial lift force scales in the range of $a^3$ to $a^6$ where "a" is the particle (or particle cluster) diameter, such that particle clusters having larger diameters than individual particles experience a much larger force than the individual particles that do not form part of a cluster. The larger inertial lift force may be used to move particle clusters out of the fluid streams adjacent to the islands that shift upward from one from one row of the array of island structures to the next. Further information on the relation between particle size and the inertial lift force may be found in Di Carlo et al., "Particle Segregation and Dynamics in Confined Flows", Physical Review Letters, 2009, incorporated herein by reference in its entirety. Second, the equilibrium position of large particles is generally farther from the wall than that of small particles, and therefore is further from the fluid extraction channel and more likely to lie on a streamline that does not shift toward the extraction channel. The large particles therefore may be retained within a given row, whereas smaller particles flowing near the island shift upward from one row of the array to next.

Thus, fractionation is accomplished by repeatedly (1) using the inertial lift force to move large particles away from a channel wall and then (2) shifting the fluid that is free of large particles into an adjacent channel. In some implementations, fractionation can also be used to sort particles from a source fluid (e.g., blood) across fluid streamlines into an adjacent destination fluid (e.g., buffer). Thus, by forming the particle clusters discussed in block 120 with reference to FIG. 1, fractionation can be used to sort a particles of a first type from a particles of a second type having a similar size as the particles of the first type (e.g., blood platelets and bacteria cells) by using larger particles of a third type (e.g., red blood cell) to form particle clusters with the particles of the first type, and then using the size dependent force to separate the particle clusters from the particles of the second type.

Figure 7:
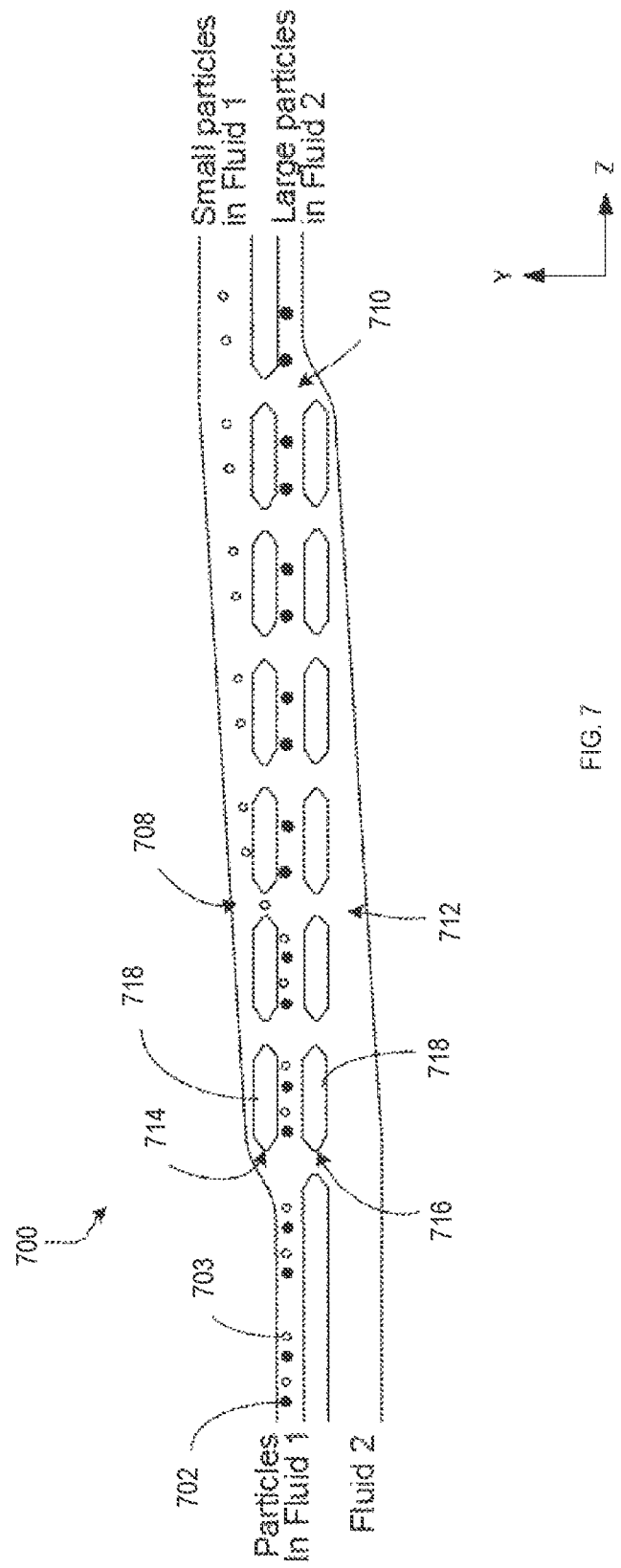
FIG. 7 is a schematic illustrating an example of a device 700 that can be used for separating particles based on size, according to one or more embodiments of the present disclosure.

For instance, FIG. 7 is a schematic illustrating an example of a device 700 that can be used for separating particles based on size, according to one or more embodiments of the present disclosure. The fluidic resistance in the third microfluidic channel 712 progressively increases due to decreasing channel width, whereas the fluidic resistance of the second microfluidic channel 708 progressively decreases due to increasing channel width. Accordingly, during operation of the device 700, repeated fluid shifting of a first fluid ("Fluid 1") from the first microfluidic channel 710 into the second microfluidic channel 708 occurs at the gaps between islands 718 in the first array 714. Similarly, repeated fluid shifting of a second fluid ("Fluid 2") from the third microfluidic channel 712 into the first microfluidic channel 710 occurs at the gaps between islands 718 in the second array 716. The fluid extraction forces are large enough to pull the small particles 703 along with the first fluid, but not great enough to counter the inertial lift forces experienced by the large particles 702 (e.g., the particle clusters). As a result, the large particles remain flowing along streamlines within the first microfluidic channel 710. After repeated particle and fluid shifting, the large particles 702 begin flowing along streamlines within the second fluid that has been shifted into the first channel 710. If the amount of fluid flowing out of channel 710 into channel 708 is kept substantially equal to the amount of fluid flowing out of channel 712 into channel 710 over the length of the particle sorting/shifting region, then the amount of fluid flowing within channel 710 can be kept substantially constant.

The microfluidic devices shown in FIGS. 3-7 implement particle shifting across fluid streamlines using inertial lift forces from the microfluidic channel walls and from the periodic arrays of island structures. Techniques other than inertial lift force can also be used to assist the shift of particles across fluid streamlines. For example, internal forces arising due to high Dean flow and/or high Stokes flow, such as inertial focusing, can be used to shift particles across fluid streamlines and/or to maintain particles within a microfluidic channel. Other size-dependent forces such as acoustic focusing, viscoelastic focusing, or dielectrophoresis, among others may be used in place of, or in addition to, inertial lift to separate or focus particles having amplified sizes. In some implementations, other external forces such as magnetic forces, acoustic forces, gravitational/centrifugal forces, optical forces, and/or electrical forces may be used in addition to the size-dependent forces to shift particles across fluid streamlines.

Additionally, the shape of the rigid island structures that separate different flow regions is not limited to the shapes shown in FIGS. 3-7. For example, the rigid island structures may have shapes similar to posts, cuboids, or other polyhedrons in which the top and bottom faces are, or can be, congruent polygons. In some circumstances, such as at high flow rates, it is advantageous to use islands with streamlined, tapered ends, as this helps minimize the formation of flow recirculations (eddies) that disrupt flow in unpredictable and undesirable ways. Other shapes for the rigid island structures are also possible. The long axis of the rigid island structures may be oriented at an angle with respect to the average flow direction of the fluid, the average flow direction of the particles, or the long axis of the sorting region. The shapes of the channel segments are not limited to the approximately rectangular shapes shown in FIGS. 3-7. The channel segments may include curves or substantial changes in width. In cross-section, the channels described in FIGS. 3-7 may be square, rectangular, trapezoidal, or rounded. Other shapes for the channel cross-sections are also possible. The channel depth may be uniform across the particle sorting region, or the channel depth may vary laterally or longitudinally.

Additionally, though FIGS. 3-7 show the microfluidic channels as approximately rectilinear pathways, the channels may be configured in other different arrangements. For example, in some implementations, the microfluidic channels may be formed to have a spiral configuration. For instance, the first microfluidic channel and the second microfluidic channel may be arranged in a spiral configuration, in which the first and second microfluidic channel are still be separated by the array of islands structures, but where the longitudinal direction of fluid flow through the channels would follow a generally spiral pathway. In some implementations, the dimensions or shape of the island structures may vary along the length of the sorting regions (e.g., in the direction of fluid flow) and/or along the width of the sorting regions (e.g., transverse to the direction of fluid flow). In some implementations, the percentage of fluid passing between island structures varies for different locations within the channel. For example, the percentage of fluid may be higher or lower through a first gap between two island structures than the percentage of fluid passing through a next adjacent gap between two island structures.

Although some implementations shown in FIGS. 3-7 include two inlet channels, additional inlet channels may be coupled to the microfluidic channels. In some implementations, three, four or more inlet channels may introduce fluid into the device regions that shift the particles through fluid exchange and inertial lift forces. For example, in some implementations, there may be three inlet channels, one which delivers blood, one which delivers staining reagents, and one which delivers a buffer stream. Using a combination of fluid shifting and inertial lift force techniques disclosed herein, white blood cells from the blood stream could be shifted into the reagent stream and then into a buffer stream.

EXAMPLES

The invention is further described in the following examples, which do not limit the scope of the invention described in the claims.

Example 1-Forming Red Blood Cell-Platelet Particle Clusters

Figure 8A:
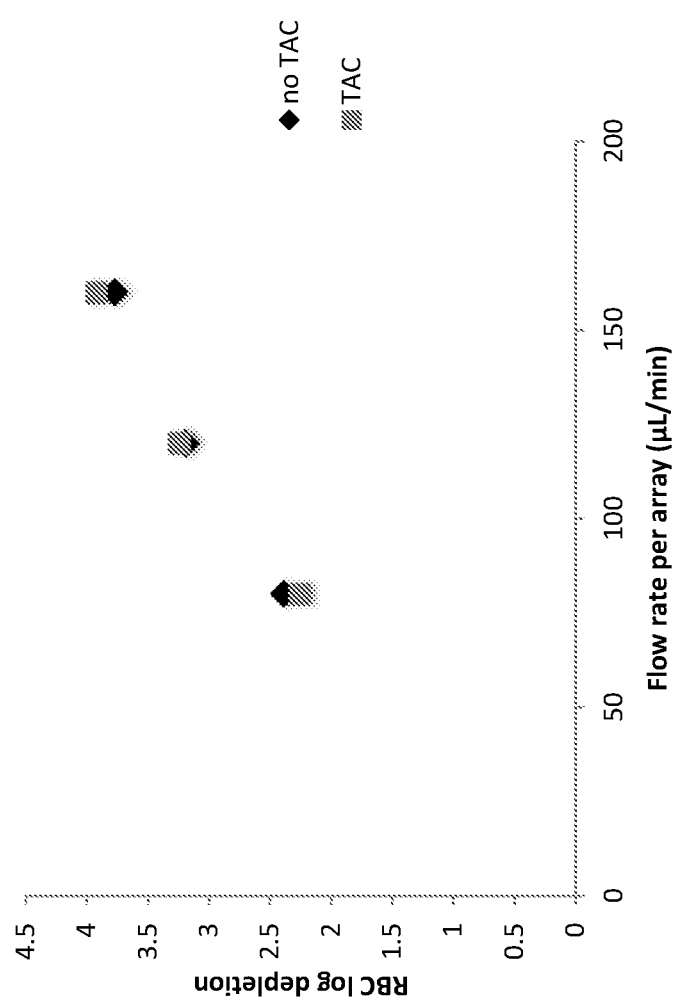
Figure 8B:
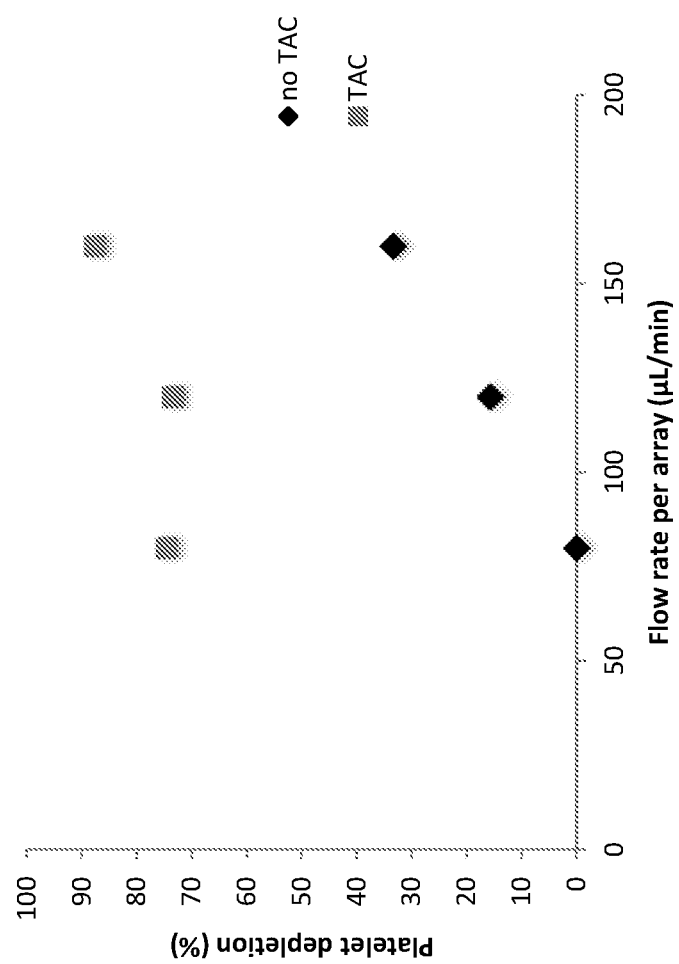

Anti-human CD235a antibody (isotype mouse IgG2a) anti-human CD41/61 (isotype mouse IgG2a), and anti-mouse IgG2a antibody (isotype rat IgG) were obtained. The antibodies (all with stock concentrations of 0.5 mg/ml) were mixed at volumetric ratios of 2 anti-mouse IgG2a: 1 anti-human CD235a: 1 anti-human CD41/61 and incubated overnight at 4C. The complexed antibodies were then brought to room temperature and incubated with whole blood (also at room temperature) to a final adjusted concentration for the anti-human CD41/61 antibody of 4.8 μg/ml. The antibodies were incubated together with the blood for 30 minutes to allow complexation of the red blood cells and platelets. Complexed blood samples were processed through a plastic microfluidic device consisting of islands in an array structure designed to effect size-based separation. The islands were 400 μm long with 3.5% siphoning of fluid between islands. Each device consisted of 3 arrays in sequence. Red blood cell and platelet depletion were compared for complexed blood (tetrameric antibody complex: TAC) and whole blood to which no antibody was added (no TAC). FIGS. 8A-8B show the relative red blood cell depletion (on a log scale in FIG. 8A) and the associated platelet depletion (FIG. 8B). The antibody complex did not affect the red blood depletion. It was found that RBC depletion was unaffected by the introduction of the antibodies to the fluid sample for forming TACs when compared to the fluid sample with no added antibodies. However, it was found that platelet depletion was achieved by forming the TACs. Platelet depletion was also impacted by the channel flow rate chosen, with more depletion at faster flow rates. Red blood cell depletion also increases with flow rate due to increased force moving the cells farther away from the channel walls.

FIG. 8C shows the results for a separate set of experiments at a single array flow rate of 80 μl/min (also in the plastic microfluidic device). This table summarizes the platelet depletion results for different blood samples (whole blood platelet counts specified). The TACs were prepared as described above and blood was incubated with the TAC at a final adjusted concentration for the anti-human CD41/61 antibody of 4.8 μg/ml, with the exception of trial 4, in which twice the amount of the antibodies was used (final concentration of 9.6 μg/ml). As shown, increasing the concentration of the antibodies did improve platelet depletion (from 60-80% to 94%). In trial 3, *Staphylococcus aureus* was spiked into the blood at a concentration of 105 CFU/ml prior to the addition of the antibody complexes and bacteria yield was subsequently quantified. The yield presented in the table accounts for bacteria loss on the chip; thus, 30% of the bacteria loss is attributable to nonspecific binding to the complexes. This loss can be mitigated through the use of antibodies without Fc domains to which bacteria are known to adhere.

Figure 9A:
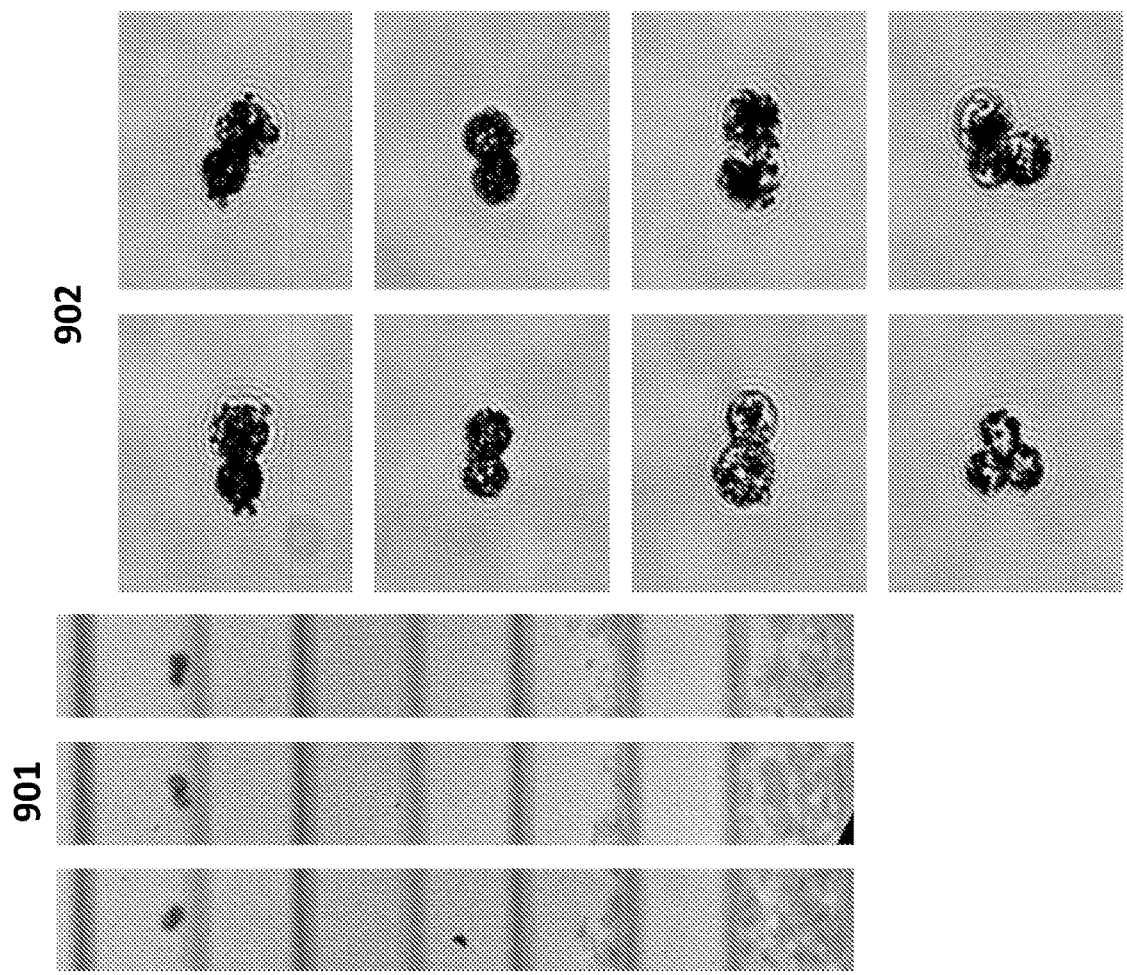

Example 2: CD45-Targeted Bead-Based Antibody-Linked White Blood Cell Clusters for Sorting FIG. 9A illustrates experiments related to size-based cell sorting based on surface marker expression. As shown, white blood cell (WBC) particle clusters were generated by processing a mixture including a solution of whole blood, biotinylated CD45 antibodies, and 1 micrometer beads through separation arrays (i.e., microfluidic device). The separation arrays included channels that were 63 micrometers wide and 65 micrometers tall, and islands that were 250 micrometers in length. 250 femtograms per WBC of biotinylated antibody (ratio of aCD45: aCD16: aCD66b was 10:1:1) were added to whole EDTA blood and incubated for 25-30 minutes at room temperature. 1 micron streptavidin dynabeads were then added to the mixture (1.8 billion per mL) and incubated for 40 minutes. After processing the mixture through the separation arrays, the resulting product fraction was enriched in white blood cell doublets (i.e., WBC-bead-WBC complexes). Cameras were used to capture images (901) of blood cells under flow and images (902) of WBC particle clusters that were sorted from smaller blood cells Example 3: Blood Type Mismatches to Generate Size-Sortable Red Blood Cell Complexes FIG. 9B illustrates experiments related to size-based cell sorting using blood group antibodies as binding moieties. As shown, two blood samples (EDTA) were mixed together at point of entry to a separation array device. One blood sample (blood sample 1) included blood of a first type and the second blood sample (blood sample 2) included blood of a second type. Anti-[second blood type] antibodies from the first sample bound red blood cells of the second type from the second sample, and anti-[first blood type] antibodies from the second sample bound red blood cells of the first type from the first sample. The mixture was processed with separation arrays using a 30 μL/min total sample flow rate and 270 μL/min buffer rate. A high speed camera was used to generate images (903) of blood cells under flow. Furthermore, images (904) were generated to capture RBC particle clusters that were sorted from smaller blood cells.

Example 4: Using Centrifugation to Generate Sortable WBC clusters in Buffy Coat

Figure 9C:
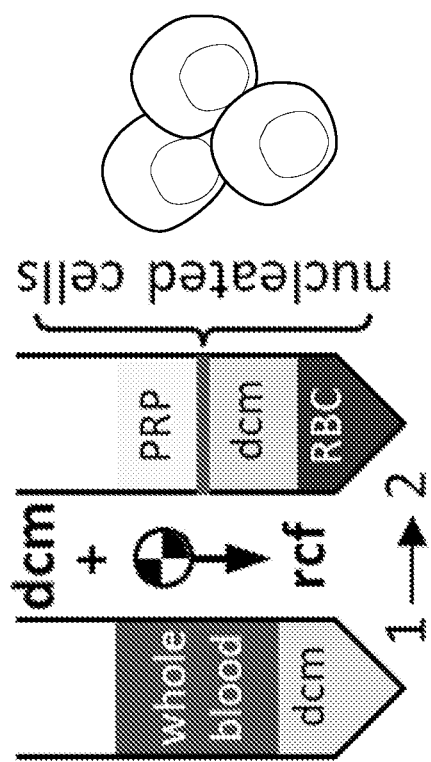

FIG. 9C illustrates experiments related to removing unwanted particle clusters from peripheral blood mononuclear cell product. Apheresis machines use continuous flow centrifugation to skim various blood components from one another by density. This allows processing of large volumes of blood while returning key blood components to the patient. However, the process brings WBCs into close proximity within a buffy coat layer, thus causing about 1-10% of WBCs to cluster. A centrifugation process designed to mimic an apheresis machine was used to process, using relative centrifugal force (rcf), a mixture of whole blood and density gradient centrifugation medium (dcm) to separate the platelet rich plasma (PRP) from the RBCs of the mixture, and generate WBC clusters. It was demonstrated that these unwanted WBC clusters can be removed from the peripheral blood mononuclear cell product, within which T cells reside, by running collected leuko-apheresis product through separation arrays.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:
1. A method comprising:
    introducing a plurality of binding moieties into a fluid sample comprising blood; allowing at least one of the plurality binding moieties to bind two or more biological particles to form a particle cluster, wherein the two of more biological particles of the particle cluster comprises a first type of biological particle bound to a second different type of biological particle, and wherein the first type of biological particle comprises a red blood cell, and wherein the second different type of biological particle comprises a platelet;
    providing a microfluidic device having a particle sorting region, the particle sorting region defining a first microfluidic channel and a second microfluidic channel; and
    flowing the fluid sample comprising the particle cluster into the particle sorting region of the microfluidic device, including dividing, using the particle sorting region, the fluid sample into a first fluid stream within the first microfluidic channel and a second fluid stream within the second microfluidic channel,
    wherein dividing the fluid sample into the first fluid stream within the first microfluidic channel and the second fluid stream within the second microfluidic channel comprises applying, using the microfluidic device, a size-dependent force within the particle sorting region that is sufficient to maintain the particle cluster within the first fluid stream and away from the second fluid stream,
    wherein the fluid sample comprises a third type of biological particle different from the first and second types of biological particles, and wherein flowing the fluid sample into the particle sorting region of the microflu- idic device comprises flowing the third type of biological particle flows from the first fluid stream into the second fluid stream in the particle sorting region, and wherein the size-dependent force within the particle sorting region is insufficient to maintain the third type of biological particle in the first fluid stream.

2. The method of claim 1, wherein an average size of the third type of biological particles within the fluid sample is smaller than a size of the particle cluster.

3. The method of claim 1, wherein an average size of the second type of biological particles within the fluid sample is smaller than a size of the first type of biological particle.

4. The method of claim 2, wherein the average size of the second type of biological particles within the fluid sample is the same as an average size of the third type of biological particle within the fluid sample.

5. The method of claim 1, wherein the particle sorting region comprises a third microfluidic channel different from the first microfluidic channel, and
wherein the method comprises flowing a second fluid sample into the third microfluidic channel, including flowing a portion of the second fluid sample from the third microfluidic channel into the first microfluidic channel in the particle sorting region, and wherein the size-dependent force experienced by the particle cluster is sufficient to drive the particle cluster from the fluid sample into the portion of the second fluid sample in the first microfluidic channel.

6. The method of claim 5, wherein the second fluid sample comprises a buffer solution.

7. The method of claim 1, wherein a first binding moiety of the plurality of binding moieties binds to the first type of biological particle and a second binding moiety of the plurality of binding moieties binds to the second, different type of biological particle, and the first binding moiety binds to the second binding moiety to form the particle cluster.

8. The method of claim 7, wherein at least one of the first binding moiety or the second binding moiety comprises an antibody or an antibody fragment.

9. The method of claim 1, wherein a first binding moiety of the plurality of moieties binds to the first type of biological particle, a second binding moiety of the plurality of moieties binds to the second different type of biological particle, and at least a third binding moiety of the plurality of moieties binds the first binding moiety to the second binding moiety of the plurality of moieties to form the particle cluster.

10. The method of claim 9, wherein at least one of the first binding moiety, the second binding moiety, or the third binding moiety comprises an antibody or an antibody fragment.

11. The method of claim 1, wherein the third type of biological particle comprises a bacteria cell.

12. The method of claim 1, wherein at least one of the plurality of binding moieties target at least one of anti-mouse IgG Fc antigens, anti-human CD41 antigens, or anti-human CD235a antigens.

13. The method of claim 1, further comprising cleaving the particle cluster when the particle cluster reaches a predefined position in the microfluidic device such that the two or more biological particles making up the particle cluster are no longer bound to each other.

14. The method of claim 13, wherein cleaving the particle cluster includes using at least one of light, an increase in temperature of the particle cluster, a decrease in temperature of the particular cluster, or a buffer composition.

15. The method of claim 1, wherein the plurality of binding moieties comprises a recombinant protein.

16. The method of claim 1, wherein the plurality of binding moieties comprises at least one of a polymer, an antibody, an antibody fragment, an aptamer, or a tetrameric antibody complex.

17. The method of claim 1, wherein the size-dependent force comprises at least one of an inertial lift force or a deterministic lateral displacement force.

18. The method of claim 1, wherein the size-dependent force comprises at least one of an acoustic force or a dielectric force.

19. The method of claim 1, wherein the fluid sample comprises the first type of biological particle, the second type of biological particle and the third type of biological particle.

* * * * *

UNITED STATES PATENT AND TRADEMARK OFFICE
CERTIFICATE OF CORRECTION

Page 1 of 1

PATENT NO. : 12,385,908 B2
APPLICATION NO. : 17/417879
DATED : August 12, 2025
INVENTOR(S) : Jon F. Edd et al.

It is certified that error appears in the above-identified patent and that said Letters Patent is hereby corrected as shown below:

In the Claims

Column 23, Line 2:
In Claim 1, after "particle" delete "flews"

Signed and Sealed this
Seventh Day of October, 2025

John A. Squires
*Director of the United States Patent and Trademark Office*